(12) United States Patent
Kowalchuk et al.

(10) Patent No.: US 10,545,163 B1
(45) Date of Patent: *Jan. 28, 2020

(54) SAMPLE EXTRACTION AND ROTATION DEVICE FOR AUTOMATED BLOOD SAMPLE PROCESSING SYSTEMS

(71) Applicant: CERNER INNOVATION, INC., Kansas City, KS (US)

(72) Inventors: Daniel Mark Kowalchuk, Port Hope (CA); Joseph Eugene Rose, Grand Blanc, MI (US); Stephen Ward, Peterborough (CA); Robert Loigner, Peterborough (CA)

(73) Assignee: Cerner Innovation, Inc., Kansas City, KS (US)

( * ) Notice: Subject to any disclaimer, the term of this patent is extended or adjusted under 35 U.S.C. 154(b) by 217 days.

This patent is subject to a terminal disclaimer.

(21) Appl. No.: 15/855,025

(22) Filed: Dec. 27, 2017

Related U.S. Application Data

(62) Division of application No. 14/986,511, filed on Dec. 31, 2015, now Pat. No. 10,209,267.

(51) Int. Cl.
| | |
|---|---|
| *G01N 35/00* | (2006.01) |
| *G01N 35/10* | (2006.01) |
| *G01N 35/04* | (2006.01) |
| *G01N 21/25* | (2006.01) |
| *G01N 21/88* | (2006.01) |

(52) U.S. Cl.
CPC ......... *G01N 35/109* (2013.01); *G01N 21/255* (2013.01); *G01N 21/88* (2013.01); *G01N 35/0099* (2013.01); *G01N 35/00871* (2013.01); *G01N 2035/1051* (2013.01); *G01N 2035/1093* (2013.01); *G01N 2201/12* (2013.01)

(58) Field of Classification Search
None
See application file for complete search history.

(56) References Cited

U.S. PATENT DOCUMENTS

| | | | |
|---|---|---|---|
| 4,121,868 A | 10/1978 | Pierce et al. | |
| 5,590,052 A | 12/1996 | Kopf-Sill et al. | |
| 5,623,415 A | 4/1997 | O'Bryan et al. | |
| 5,692,220 A | 11/1997 | Diamond et al. | |

(Continued)

FOREIGN PATENT DOCUMENTS

WO 2015002218 A1 1/2015

OTHER PUBLICATIONS

Non-Final Office Action received for U.S. Appl. No. 14/986,392, dated Aug. 13, 2018, 52 pages.

(Continued)

*Primary Examiner* — Kathryn Wright
(74) *Attorney, Agent, or Firm* — Shook, Hardy and Bacon LLP

(57) ABSTRACT

Systems, methods, devices, and apparatus for detecting sample defects in blood samples processed in automated processing systems are described herein. One aspect describes an automated blood sample processing apparatus having a pre-analytic specimen integrity monitoring device. Another aspect describes devices, systems, and methods for identifying blood components and properties in blood samples. Further aspects relate to systems and methods for setting reference ranges for sample defects and interference in blood samples. Additionally, devices, systems, and methods for identifying defective samples are described.

6 Claims, 17 Drawing Sheets

(56) References Cited

U.S. PATENT DOCUMENTS

| | | | |
|---|---|---|---|
| 5,879,628 | A | 3/1999 | Ridgeway et al. |
| 8,028,816 | B1 | 10/2011 | Smith et al. |
| 10,267,813 | B1 | 4/2019 | Bhatia et al. |
| 10,311,569 | B1 | 6/2019 | Bhatia et al. |
| 2003/0138140 | A1 | 7/2003 | Marcelpoil et al. |
| 2003/0139903 | A1 | 7/2003 | Zweig et al. |
| 2004/0005245 | A1 | 1/2004 | Watson et al. |
| 2004/0018528 | A1 | 1/2004 | Morimoto et al. |
| 2004/0066978 | A1 | 4/2004 | Nanbu |
| 2004/0204910 | A1 | 10/2004 | Brumbach et al. |
| 2005/0051466 | A1 | 3/2005 | Carter et al. |
| 2005/0163354 | A1 | 7/2005 | Ziegler |
| 2005/0196867 | A1 | 9/2005 | Bower et al. |
| 2006/0188140 | A1 | 8/2006 | Gholap et al. |
| 2007/0172388 | A1 | 7/2007 | Padmanabhan et al. |
| 2007/0177778 | A1 | 8/2007 | Massaro |
| 2009/0142844 | A1 | 6/2009 | Le Comte |
| 2010/0027868 | A1 | 2/2010 | Kosaka et al. |
| 2010/0111767 | A1 | 5/2010 | Yonekura et al. |
| 2011/0089709 | A1 | 4/2011 | Neeper |
| 2011/0200239 | A1 | 8/2011 | Levine et al. |
| 2012/0140230 | A1 | 6/2012 | Miller |
| 2012/0309636 | A1 | 12/2012 | Gibbons et al. |
| 2013/0082099 | A1 | 4/2013 | Furrer |
| 2013/0129166 | A1 | 5/2013 | Miller et al. |
| 2013/0171681 | A1 | 7/2013 | Shibata |
| 2014/0233826 | A1 | 8/2014 | Agaian et al. |
| 2015/0241457 | A1 | 8/2015 | Miller |
| 2015/0369832 | A1 | 12/2015 | Sacco |
| 2016/0109350 | A1 | 4/2016 | Esaki et al. |
| 2016/0266157 | A1 | 9/2016 | Suzuki et al. |

OTHER PUBLICATIONS

Non-Final Office Action received for U.S. Appl. No. 14/986,432, dated Aug. 15, 2018, 35 pages.

Notice of Allowance received for U.S. Appl. No. 14/986,511, dated Aug. 28, 2018, 16 pages.

Non-Final Office Action received for U.S. Appl. No. 14/986,505, dated Jul. 18, 2019, 16 pages.

Rubner et al., "Empirical Evaluation of Dissimilarity Measures for Color and Texture", Computer Vision and Image Understanding, vol. 84, 2001, pp. 25-43.

Preinterview First Office Action received for U.S. Appl. No. 14/986,505, dated Sep. 27, 2018, 4 pages.

Non-Final Office Action received for U.S. Appl. No. 14/986,321, dated Dec. 4, 2018, 28 pages.

Oshima et al., "Optical Measurement of Blood Hematocrit on Medical Tubing with Dual Wavelength and Detector Model," 31st Annual International Conference of the IEEE EMBS, IEEE, Sep. 2009, pp. 5891-5896.

Final Office Action dated Mar. 21, 2018 in U.S. Appl. No. 14/986,432, 30 pages.

Final Office Action dated Apr. 13, 2018 in U.S. Appl. No. 14/986,392, 37 pages.

Final Office Action dated May 4, 2018 in U.S. Appl. No. 14/986,321, 15 pages.

Final Office Action received for U.S. Appl. No. 14/986,505, dated Feb. 21, 2019, 17 pages.

First Action Interview Office Action received for U.S. Appl. No. 14/986,505, dated Nov. 19, 2018, 6 pages.

US 10,545,163 B1

SAMPLE EXTRACTION AND ROTATION DEVICE FOR AUTOMATED BLOOD SAMPLE PROCESSING SYSTEMS

CROSS-REFERENCE TO RELATED APPLICATIONS

This application a divisional of U.S. application Ser. No. 14/986,511, entitled "SAMPLE EXTRACTION AND ROTATION DEVICE FOR AUTOMATED BLOOD SAMPLE PROCESSING SYSTEMS," filed Dec. 31, 2015, which is related by subject matter to U.S. patent application Ser. No. 14/986,321, entitled "Specimen Integrity Monitoring Device for Automated Blood Sample Processing Systems," filed Dec. 31, 2015; Ser. No. 14/986,392, entitled "Identifying Liquid Blood Components From Sensed Data to Monitor Specimen Integrity," filed Dec. 31, 2015; Ser. No. 14/986,432, entitled "Monitoring Specimen Integrity in Automated Blood Sample Processing Systems," filed Dec. 31, 2015; and Ser. No. 14/986,505, entitled "Establishing Reference Ranges and Determining Results for Samples Processed by a Specimen Integrity Monitor," filed Dec. 31, 2015. Each of the aforementioned applications is assigned or under obligation of assignment to the same entity as this application, and incorporated in this application by reference.

BACKGROUND

Traditionally, blood processing involved several individuals that handled a given sample. Accordingly, prescreening of samples was typically performed manually. However, as systems have moved toward automation, fewer individuals handle the samples and, as a result, opportunities for manual visual inspection of samples have decreased. Automated systems for processing blood samples have failed to provide an adequate mechanism for prescreening defective samples. Consequently, improperly labeled specimens, improperly collected specimens and specimens with various types of sample interference are commonly processed in current automated systems. Accordingly, current system often process defective samples, resulting in sample errors and/or inaccurate results.

SUMMARY

Embodiments herein generally relate to devices, apparatus, systems, and methods for monitoring for and detecting defective samples in automated blood sample processing system. In one aspect, a sample tube gripping and rotation device for use in an automated blood sample processing system is described herein. Additionally, a sample tube gripping and rotation device for use in a specimen integrity monitor is provided herein.

BRIEF DESCRIPTION OF THE DRAWINGS

Illustrative embodiments of the present invention are described in detail below with reference to the attached drawing figures, which are incorporated by reference herein and wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different features or combinations of features similar to the ones described in this document, in conjunction with other present or future technologies. Although the terms "step" and/or "block" might be used herein to connote different elements of methods employed, the terms should not be interpreted as implying any particular order among or between various steps herein disclosed unless and except when the order of individual steps is explicitly stated.

As briefly discussed hereinabove, aspects of this disclosure generally relate to detecting defects in blood samples processed in an automated processing system(s). This disclosure provides devices and systems that allow a defective sample to be automatically identified before it is processed.

At a high level, automated systems include sample routing tracks for moving samples throughout the system. The system may have an automated system control (which will generally be designated hereinafter as an "ASC") for controlling routing parameters associated with samples. The routing parameters may be set based on sample type. For example, a coagulant sample may only be routed to a coagulometer, while a complete blood count sample, or serum for biochemical testing, may be routed through several analyzers. Accordingly, the ASC may operate, in part, to send a sample to the appropriate analyzers. Accordingly, a sample may be routed to a specimen integrity monitor (which may be referred to as a "SIM"), based on routing parameters associated with the sample. The SIM generally operates to detect bad samples before they get to the analyzers.

The SIM may identify defective samples using captured sensor information to determine properties associated with the sample. A variety of sensors may be used to capture the information necessary to identify blood properties and defects. For example, the sensors may include highly color sensitive cameras. Accordingly, the sensors may include a red color detector, a blue color detector, and a green color detector, for detecting color elements for the sample, among others. The sensed information from the sensors is then sent to one or more specialized processors to determine sample properties and defects.

Processing Sensed Information to Determine Sample Properties

Figure 2:
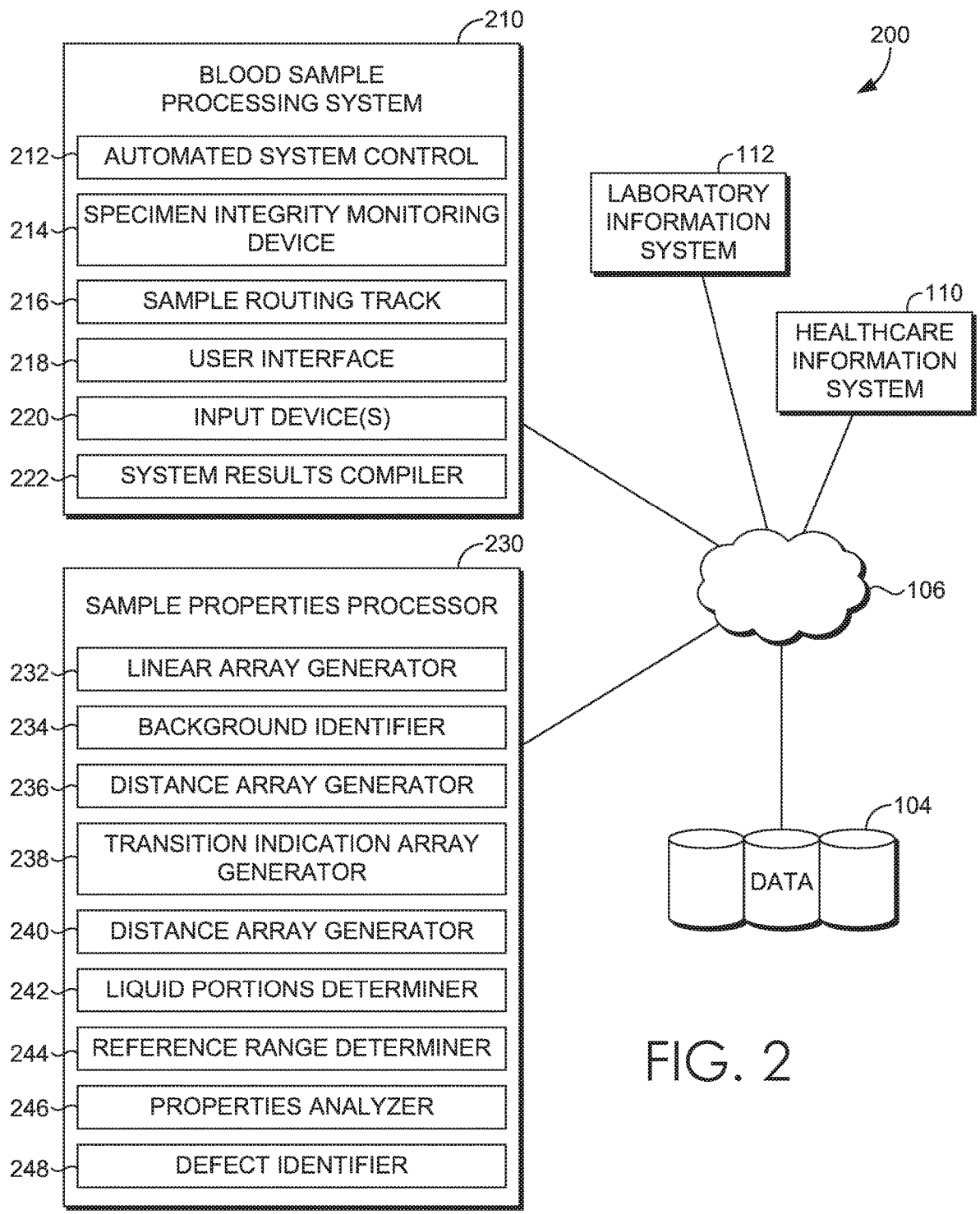
FIG. 2 is a block diagram that depicts aspects of a computing system suitable for processing blood samples to determine sample properties and defects, in accordance with some aspects herein.

Having provided the general context in which the embodiments disclosed herein employed, more particular aspects of the systems and methods for determining sample defects will be addressed. FIG. 2 shows an exemplary computing system 200 for processing samples to determine sample properties and defects.

Liquid components or portions of blood have a corresponding colors and/or ranges of colors. Distances and linear space may be used to determine how far apart color elements are, as a proxy for identifying differences between colors in a blood sample. As a result, liquid components of a sample may be identified by breaking the color elements of the sample into color arrays. Values for the color arrays may then be used to determine a variety of types of interference or defects for the sample.

The system 200 may include a sample properties processor 230 that is configured to detect sample properties and identify liquid components of blood samples. The sample properties processor 230 may receive, from the one or more sensors, a plurality of color elements for a sample. In some aspects, the plurality of color elements comprises one or more channel values. The channel values may include a red channel value; a blue channel value; and a green channel value ("RBG" values). The channel values may be communicated by the sensors as a telegram, with delimiters for separating the RBG values. In one aspect, the sensors send a string of ASCII characters through Ethernet, as defined by telegram settings. The color elements may then be stored for further processing.

A linear array generator 232 may generally be configured for creating a linear array of the color elements. The linear array generator 232 may map the color elements as a straight line, in order to determine a distance between the color elements. Euclidean distance is the straight-line distance between two points in Euclidean space. For example, the Euclidean distance between points p and q is length of line segment connecting them. Using the RBG channel values, the distance between colors may be determined. Further, the linear array generator 232 may create a digital record of the plurality of color elements as a linear array.

As can be appreciated, although using Euclidean distance is one way of determining differences or deviations between color elements (which may also be described as data elements having values corresponding to a hue or intensity of RBG values), any other suitable means for determining color transitions is contemplated within the scope of the present disclosure. For example, a Chebyshev distance, a Mahalanobis distance, and variations thereof for determining distances or deviations between vectors or arrays, should be considered within the scope of the embodiments described herein.

The sample properties processor 230 may also include a background identifier 234 for determining one or more background color elements of the linear array. At a high level, the background identifier 234 may generally be responsible for determining and removing background color elements from the linear array. In one aspect, the one or more background color elements are outside of a predetermined range of valid color elements. The background elements may be color elements having a brightness outside of a predetermined valid brightness range.

Background color elements may be present in the sensed data due to shadows, sample barcodes, or ultraviolet light. Generally speaking, background color elements are color elements that do not occur within a blood sample and/or sample tube. Accordingly, in order to generate accurate color arrays for a sample, the background color elements should be removed. In one example, starting with the first color element of the linear array, each color element may be analyzed to determine a first color element within the valid brightness range. Continuing with this example, once the first valid color elements has been determined, the linear array is analyzed from the opposite end to determine a first color element within the valid brightness range. By way of illustration, the linear array may be analyzed from left to right for a first loop and from right to left for a second loop. Accordingly, any color elements outside of the valid brightness range may be trimmed or otherwise removed from the linear array, because they correspond to color elements that are not a part of the sample being analyzed. The remaining color elements of the of the linear array may then be stored as a clean array, which no longer includes background colors or empty tube regions.

A distance array generator 236 may generally be responsible for determining a distance between each color element of the clean array. The distance between each color element may be determined using similar means to those used to determine the initial linear array. For example, a Euclidean distance between each color element may be determined. However, because noise/background color elements have been removed, the distance between color elements now includes only color elements for the sample tube contents.

The distances determined by the distance array generator 236 may be stored as a distance array.

A transition indication array generator 238 may generally operate to determine color transitions using the distances determined by the distance array generator 236. In one example, the transition indication array generator 238 compares each distance to a transition indication threshold. When a distance is determined to be above the transition indication threshold, the transition indication array generator 238 indicates a color transition. In one aspect, a Boolean array with a size of n−1 may be generated. In this example, n is the size of the distance array, or the linear array without outliers/background color elements. Accordingly, when a difference between one color element and a subsequent color element is above the threshold, the location may be marked in an index of the Boolean array as true. The transition indication array generator 238 may also operate to store the determined transitions as a transition indication array.

In some aspects, the transition indication array generator 238 may also operate to detect the presence of a barcode. Because a barcode has numerous dark and light regions in close proximity to one another, a barcode will result in a high number of transitions indications. In one aspect, the transition indication array generator 238 may compare the total number of transitions in the array to the number of color elements in the array. The resulting value may then be compared to a threshold to determine a presence of a barcode. Accordingly, when the transitions indicate the presence of a barcode, the values corresponding to the barcode may be removed from the transition indication array in order to eliminate the barcode transitions from the transition indication array. Additionally, the values and color elements corresponding to the barcode may be stored and used to identify the sample.

In additional aspects, a color boundary detector 240 may operate to determine one or more boundary regions. In general, the transition from one color to another in blood samples is gradual, because the liquid portions mix together and form an intermediate color. The transition indication array may contain a number of transitions close to one another, that in actuality comprise a single color transition. When transition indications are above a predetermined frequency for a portion of the array, the portion of the array containing the high frequency of transitions may be designated as a boundary region.

Boundary regions may be detected, for example, by determining if another transition indication is within the next four color elements of the array. If another transition indication is found within the next four elements, the transition indication is removed. The color boundary detector 240 may determine a boundary region midpoint for each boundary region. The boundary regions may then be mapped as a single color transition, at the boundary region midpoint, in the transition indication array. This may be done iteratively. That is, a first transition indication may be determined, a second transition indication may be determined two color elements away, and a third transition indication may be four color elements away from the second transition indication. Continuing with the Boolean array example from above, each of the first, second and third transition indications are set to false. However, the color element at the midpoint between the first transition and second transition may be set as true. Accordingly, in this example, the boundary region, or region containing a mixture of two liquid blood components has been indicated as a single transition, rather than three separate transitions. As a result, the transition indication array may be generated and indicated as an array that represents actual transitions between the components/portions of the sample.

A liquid portions determiner 242 may generally operate to cut (or otherwise separate) the transition indication array at each color transition to create a number of color arrays. Each color array corresponds to a liquid portion or component of the blood sample. This is so because each blood component, at a granular level, has a discrete range of color values. As described above, the transition indication array may now be an array without background color elements and an array, which has each transition indication marked.

In one example, the transition indication array may be separated at each transition indication to form a number of individual color arrays. Each color element of the color array may have an associated color value, which may be the RBG values of the color elements. Accordingly, each color array has a range of color values which corresponds to a liquid portion of the blood sample.

Determining a color value for the color arrays may be accomplished in several ways. In one aspect, the color element in the middle of each color array may be determined and used as a color value for the color array. Additionally, some color arrays may still contain mixture of two liquid portions due to the boundary regions discussed above. In one aspect, if the size of the array is above a threshold, color elements may be trimmed from either end of the array and discarded. The color array may be trimmed repeatedly until the array is a predetermined size.

Further, in some aspects, the liquid portions determiner 242 may be configured to determine an average or merged color for each color array. The majority of the true color of a given liquid blood component may be located in the middle of a given color array. The merged color may also be determined by generating a normal distribution weighted average of the one or more color elements of the color array. The merged color value may be used as the color value for the color array and corresponding blood component.

Accordingly, using any of the above mechanisms, a number of color arrays for each sample processed by the sample properties processor 230 may be determined. Further, each color array has a color value corresponding to a liquid blood property of the sample.

Generating Reference Ranges

The SIM may also be utilized to generate reference ranges for potential sample defects. Reference ranges may be used by the SIM to define an acceptable range of color values for liquid portions of the sample. The sample properties processor 230 may include a reference range determiner 244, which generally operates to set reference range boundaries and generate the reference ranges. The values used for the reference range boundaries may be determined based on color arrays for reference samples. The color arrays may be determined in the same manner as detailed above.

Reference samples correspond to a testable criteria, or defect, associated with a liquid portion of the sample. For example, as will be discussed in more detail below, the testable criteria may include one or more of: a hematocrit criteria; a hemolysis criteria; a clotting criteria; an icterus criteria; and a lipemia criteria. The reference samples may have a predetermined minimum or maximum sample criteria value for samples analyzed in the automated blood sample processing system 210. For example, a reference sample may be fully analyzed to determine a hematocrit value that represents a lower limit of hematocrit values for acceptable samples. As will be appreciated, reference samples may also correspond to mean, median, or any other gradient indicator for acceptable sample. In other aspects, a visual inspection of the reference sample may indicate that the sample is an ideal sample for a minimum or maximum amount of red blood cells for acceptable samples.

Accordingly, a plurality of color elements for a first reference sample may be sensed by the one or more sensors and communicated to the sample properties processor 230. Color arrays for the first reference sample may then be determined, as detailed above. A color array that corresponds to the testable criteria may then be identified. The identified color array may be used by the reference range determiner 244 to establish a first reference range boundary. As can be appreciated, the first reference range boundary has a corresponding color value, based on the color array. The first reference range boundary may represent the minimum acceptable value. Accordingly, a second reference sample may be processed in the same way to determine a second reference range boundary corresponding to the maximum acceptable value. The reference range determiner 244 may then generate a reference range for the testable criteria, based on the reference range boundaries.

Further, complete images of the reference samples may be stored and later accessed, for example, for comparison to a sample. The reference range determiner 244 may also generate a gradient or linear distribution of acceptable samples. Further, as can be appreciated, any number of samples may be run to establish reference range boundaries, medians, or any other reference range values. For example, 10 reference samples may be analyzed to determine a minimum reference range boundary. Continuing with this example, a mean color value, or a mean of the color array values for the 10 reference samples may be used as the color value for the reference range boundary.

Sample Processing

Actual patient samples may be analyzed for defects, for example, by the blood sample processing system 210, as shown in FIG. 2. The blood sample processing system 210 may include the ASC 212, which may route a given sample to the SIM 214, based on routing parameters associated with the sample in the ASC 212. Samples may be routed to the SIM 214 based on any number of criteria. For example, potassium assays are particularly sensitive to hemolysis. Accordingly, a patient sample that is being analyzed for potassium levels may automatically be routed to the SIM 214. As can be appreciated, particularly in total lab automation systems, it may be desirable to route each sample to the SIM 214 in order to provide a mechanism for prescreening the samples for visible defects.

Samples may be analyzed using the mechanisms detailed above, and may employ many of the same components as described above to do so. For example, the one or more sensors may capture a plurality of images of the sample, and associated data elements. A plurality of color elements for the sample may be determined from the images. Accordingly, the color elements may be used to generate one or more color arrays for the sample, as described above. Further, the plurality of color elements may be used to determine a tube cap color for the sample. The tube cap color may be determined, for example, by a sample tube features determiner 246, which may also be configured to determine a sample tube size.

Additionally, the sample properties processor 230 may determine a sample type corresponding to the cap color. A given tube cap color may be associated with a specific type of sample. For example, a light blue tube cap may be associated with a hematocrit sample type. Continuing with this example, because the sample type is a hematocrit sample type, it may be determined that only defects that cause interference with a hematocrit sample need to be determined. Accordingly, the sample properties processor 230 may determine color arrays and use reference ranges that are associated with the specific defect. Associations between cap colors and sample types may be stored in, for example, the ASC 212. Additionally, the associations may be communicated to and stored by the sample properties processor 230.

The sample tube features determiner 246 may also be responsible for determining the barcode information from a barcode on the sample. The sample properties processor 230 may also use the barcode information to retrieve a sample type for the sample. The sample properties processor 230 may also compare the sample type and corresponding tests associated with a sample based on the barcode information, with the sample type indicated by tube cap color and tube size determined by the sample tube features determiner 246. Accordingly, a sample that has been placed in an incorrect sample tube may be identified by the SIM 214 and indicated as defective.

Additionally, in aspects herein, a complete image of the sample and a digital record of all data elements associated with the sample may be generated by the sample properties processor 230 and communicated to the ASC 212. Although referred to as a processor, the sample properties processor 230 may have a dedicated local memory, or other suitable data structure. Accordingly, sample data elements and result information may also be stored locally by the sample properties processor 230.

The sample properties processor 230, and its subcomponents, may determine color arrays and associated liquid portions of the sample. The color arrays may be determined based on the plurality of color elements, as described hereinabove. Based on the sample type, the sample properties processor 230 may retrieve reference ranges for defects that will be analyzed. Accordingly, a defect identifier 248 may compare the determined color arrays for the sample, and associated values, to the reference ranges for a defect. As can be appreciated, when a color array is outside of the reference range, a defect may be indicated.

Just as sample types may have associated defects, each sample type may also require a minimum volume to perform a valid test. Accordingly, a minimum volume for each sample type may be predetermined and stored for comparison to samples. The defect identifier 248 may also operate to determine if the liquid volume of the sample is adequate. The volume of the sample may be determined, for example, by a sample tube features determiner 246. Determining the liquid volume of the sample may include identifying gel barriers; anticoagulants; serum; as well as any other substance in the sample tube other than the liquid blood. Accordingly, the liquid volume of the sample may include the tube volume less a volume of any substance that is not a liquid blood sample. The liquid volume of the sample determined by the sample tube features determiner 246 may be compared to the minimum by the defect identifier 248. Additionally, the sample tube features the 246 may be configured to detect a presence of air bubbles in the sample. Air bubbles may be present in improperly centrifuged samples and may cause interference in a variety of instruments.

Accordingly, when a defect is identified, the indication may be communicated to the ASC 212, which may route the sample to an error or defect holding lane. Further, all data elements associated with the sample and the identified defect may be communicated to the ASC 212 and any other aspects of the system via a network 106. The sample and defect information may be retained indefinitely or for a customizable of time for additional comparison and analysis.

Types of Sample Defects

Defects and errors associated with blood samples may be caused by improper collection, handling, and processing prior to analysis, among many other potential causes. Further, physiologic patient variables, such as increased or excessive amounts of a given blood component in a patient's blood, may also cause the sample defects. Processing samples with defects may lead to a sample error, which is only determined after a full analysis of the sample has been completed. Further, processing defective samples may also lead to inaccurate test results. Accordingly, processing defective blood samples may lead to unnecessary and potentially inappropriate patient care, and increased costs due to analyzing bad samples.

In one aspect, the sample properties processor 230 may analyze the sample to determine a level of hemolysis in the sample. When blood samples are improperly processed or handled, hemolysis may occur. Hemolysis causes red blood cells to rupture and release cytoplasm into surrounding fluids. The presence of hemolysis may or may not compromise a sample depending on the type of test intended for the sample. Accordingly, a range of hemolysis that is acceptable may be set based on the sample type and compared to the level of hemolysis in the sample to determine if the sample is defective.

Additionally, the sample properties processor 230 may determine a percentage of red blood cells of the total sample volume, or a hematocrit value. The system may be configured to define an acceptable hematocrit value, so that the sample hematocrit value may be compared to a defined range. Based on the comparison, samples may be rejected or routed for continued testing. Further, based on the color arrays generated for a sample, unacceptable levels of clotting may be detected. For example, the sample properties processor 230 may detect visible clots, including red cell clots in whole blood, or fibrin clots in plasma.

Additionally, the sample properties processor 230 may analyze the sample for an icterus defect. Icteric plasma contains high levels of bilirubin. Icteric plasma samples have a high prevalence in samples from intensive care unit, gastroenterology, surgical, and pediatric patients. High concentrations of bilirubin can interfere with coagulation and other types of tests. Visible detection of icteric samples is sometimes difficult. The sample properties processor 230 may detect icteric samples prior to full testing in order to avoid testing a sample with interference, which may result in an error. Further, the sample properties processor 230 may detect visible lipemia, or turbidity due to elevated concentrations of lipids. Lipemia usually translates to a triglyceride level >1000 mg/dL (whole blood) or >300 mg/dL (serum or plasma). Accordingly, reference ranges may be set at color values that correspond to these to the concentrations above.

Further, the sample properties processor 230 may determine if a sample has an inadequate volume. Using the sensed data, the sample properties processor 230 can determine a tube size and sample type. In one example, a cap color for the tube can be determined and used to detect a type of sample being analyzed. The cap color may indicate the sample type, which may be stored in the ASC 212 and accessed by the sample properties processor 230. Gel barriers, serum and anticoagulant within the tube may be detected. Additionally, the sample properties processor 230 may determine where the top of the blood sample is, and based on the gel barriers, serum and anticoagulant, and sample type, determine whether the volume is adequate for the particular sample type. Additionally, in some aspects, the sample properties processor 230 may determine locations of plasma and whole blood within a sample tube.

Post-Processing Analytics

The blood sample processing system 210 may also include a user interface 216 to present information relating to sample defects and overrides of the defects by a technologist. Additionally, the blood sample processing system 210 may include one or more input devices 218 for receiving inputs from the technologist. Further, the blood sample processing system 210 may include a system results compiler 220 that generally operates to generate statistics and information relating to processed samples.

The system results compiler 220 may determine system results a number of samples processed by the sample properties processor 230. As can be appreciated, this may be accomplished in a number of ways. In one aspect, the sample properties processor 230 may store and/or communicate indications of each sample processed. For example, a sample properties processor 230 may have access to a local storage device, and may communicate a number of samples processed to the ASC 212, or to a laboratory information system 112, or healthcare information system 110, via the network 106. Accordingly, the system results compiler 220 may access the stored information for processed samples in order to compile results.

Further, the system results compiler 220 may determine how many of each type of defect has been identified by the SIM 214. Using means similar to those described immediately above, the system results compiler 220 may access data elements, stored indications, complete sample images, color values, and any number of other information associated with samples identified as defective. For example, when a defect is detected in a sample, the sample may be held for manual review by a technologist. In some aspects, the technologist must scan a badge or identification card using input device or the user interface 216. Further, as a technologist performs their review of samples, the identifications of the samples may automatically be associated with the technician. Accordingly, when a given technician overrides the sample properties processor's 230 determination that a sample is defective and routes the sample for continued processing, the override automatically be associated with the technician and the sample. Further, in some aspects, when an override command is received, the plurality of sample images, color values, color arrays, specimen variables, and any other information associated with the sample, may be flagged and stored with an indication that the sample was associated with an override.

By compiling sample results, particularly for samples associated with overrides, the overall system may be improved. This is so, in one aspect, because tracking overrides essentially provides an ongoing mechanism for quality control regarding determinations made by the SIM 214 and sample properties processor 230. Further, in some aspects, the user interface 216 generates and displays an image comparison screen for comparing the one or more images of a sample to a plurality of reference images. This can be an effective way of providing a real-time comparison of a sample with references and/or standards. For example, an image of a sample may be presented in a format that allows the technician to zoom in on the sample to obtain an optimal view of a sample color or colors.

Further, in some aspects, color values associated with the color arrays and corresponding blood properties or defects may be displayed with the sample images. This may also provide another quality control opportunity. For example, if a color value associated with a sample determined to be defective is visibly incorrect from the perspective of the technologist, the technologist's override of the defect may indicate that reference ranges for the defect should be adjusted. Additionally, compiling results for override may provide an indication that one of the sensors, or other physical components associated with the system needs to be inspected.

Further, in some aspects, the user interface 216 generates and displays one or more modifiable reference ranges. In one aspect, the one or more images and/or color values for a sample may be added to a reference range upon user selection. For example, a stored image for a processed sample may represent an ideal sample for setting a reference range boundary. The system provides a mechanism for adding the sample images and determined data elements to an existing reference range or may use the images and/or data elements to establish a new reference range.

Exemplary Operating System Environment

Some aspects of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

As one skilled in the art will appreciate, embodiments of the present invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media devices.

Computer-readable media include both volatile and nonvolatile media, removable and non-removable media, and contemplate media readable by a database, a switch, and various other network devices. By way of example, and not limitation, computer-readable media comprise media implemented in any method or technology for storing information, including computer storage media and communication media. Examples of stored information include computer-useable instructions, data structures, program modules, and other data representations. Computer storage media examples include, but are not limited to, information-delivery media, RAM, ROM, EEPROM, flash memory or other memory technology, CD-ROM, digital versatile discs (DVDs), holographic media or other optical disc storage, magnetic cassettes, magnetic tape, magnetic disk storage, other magnetic storage devices, and other computer hardware or storage devices. These technologies can store data momentarily, temporarily, or permanently.

While aspects of the present invention may be performed by special purpose computing devices (e.g., a sample properties processor 230 as described in detail below), the special purpose devices may be operational with general purpose devices and/or network configurations. Examples of well-known computing systems, environments, and/or configurations that may be suitable for use with the present invention include, by way of example only, personal computers, server computers, handheld or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Figure 1:
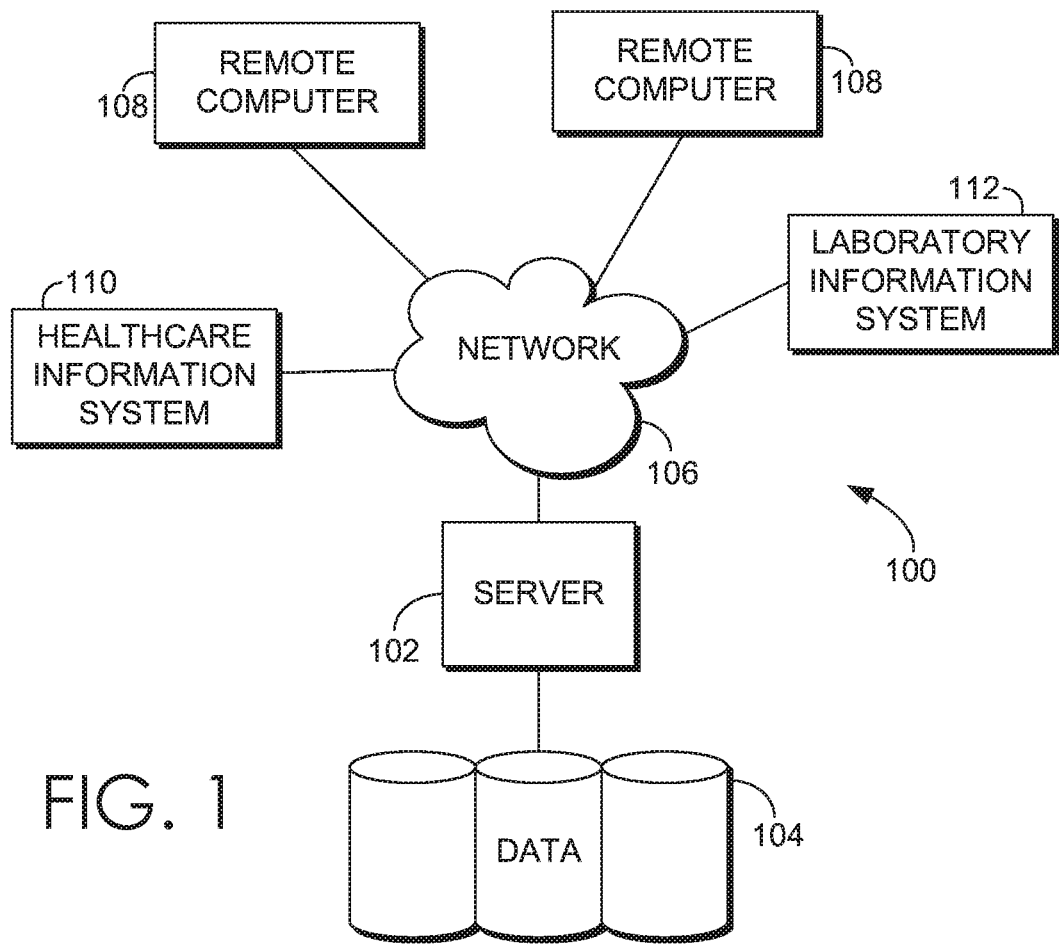
FIG. 1 is a block diagram that depicts aspects of an operating system environment suitable for practicing an embodiment of the invention.

Referring to the drawings in general, and initially to FIG. 1 in particular, an exemplary computing system environment, on which embodiments of the present invention may be implemented is illustrated and designated generally as reference numeral 100. It will be understood and appreciated by those of ordinary skill in the art that the illustrated computing system environment 100 is merely an example of one suitable computing environment and is not intended to suggest any limitation as to the scope of use or functionality of the invention. Neither should the computing system environment 100 be interpreted as having any dependency or requirement relating to any single component or combination of components illustrated therein.

With continued reference to FIG. 1, the exemplary computing system environment 100 includes a general-purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of devices capable of storing computer-readable media, for instance, database cluster 104. Computer-readable media can be any available media that may be accessed by server 102, and includes volatile and nonvolatile media, as well as removable and non-removable media. Computer-readable media may be physically stored on any number of devices and/or data structures. By way of example, and not limitation, computer-readable media may include computer storage media and communication media. Computer storage media may include, without limitation, volatile and non-volatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its evaluation criteria set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 104, provide storage of computer-readable instructions, data structures, program modules, and other data for the server 102. The server 102 may operate in a computer network 106 using logical connections to one or more remote computers 108. Remote computers 108 may be located at a variety of locations so that any number of devices and device types may be capable of integration on the network. The remote computers 108 may be personal computers, mobile devices, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are within the scope of this disclosure.

Exemplary computing system environment 100 may include a healthcare information system 110. The healthcare information system 110 may operate to store, receive, produce and communicate data elements related to the provision of healthcare. For example, the healthcare information system 110 may receive orders, such as those for laboratory testing of patient blood samples. The orders may be received from clinicians. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 may have access to the healthcare information system 110. The remote computers 108 might be personal computers, servers, routers, network PCs, peer devices, other common network nodes, or the like and might comprise some or all of the elements described above in relation to the control server 102. The devices can be personal digital assistants or other like devices.

Additionally, the exemplary computing system environment 100 may include a laboratory information system 112. The laboratory information system 112 may operate to facilitate laboratory processing of the patient blood samples ordered in healthcare information system 110. For example, in one aspect, the laboratory information system 112 may receive an indication when a laboratory test is ordered for a patient. For example, when a complete blood panel is ordered for a patient, the laboratory information system 112 may receive a notification that the complete blood panel has been ordered. Additionally, when a sample is collected, the healthcare information system 110 may communicate an indication of a sample identification number or other indication of an identity of the sample and ordered tests associated with the sample. Accordingly, the laboratory information system 112 may communicate the indication to the ASC 212, which as discussed hereinabove, may route the sample for laboratory analysis according to the ordered tests.

In some embodiments, laboratory information system 112 is a computing system made up of one or more computing devices. In an embodiment, laboratory information system 112 includes an adaptive multi-agent operating system, but it will be appreciated that laboratory information system 112 may also take the form of an adaptive single agent system or a non-agent system. Laboratory information system 112 may be a distributed computing system, a data processing system, a centralized computing system, a single computer such as a desktop or laptop computer or a networked computing system.

In an embodiment, laboratory information system 112 is a multi-agent computer system with agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control, which promotes the concept of autonomy.

Specimen Integrity Monitoring in an Automated Blood Sample Processing Apparatus

Figure 3:
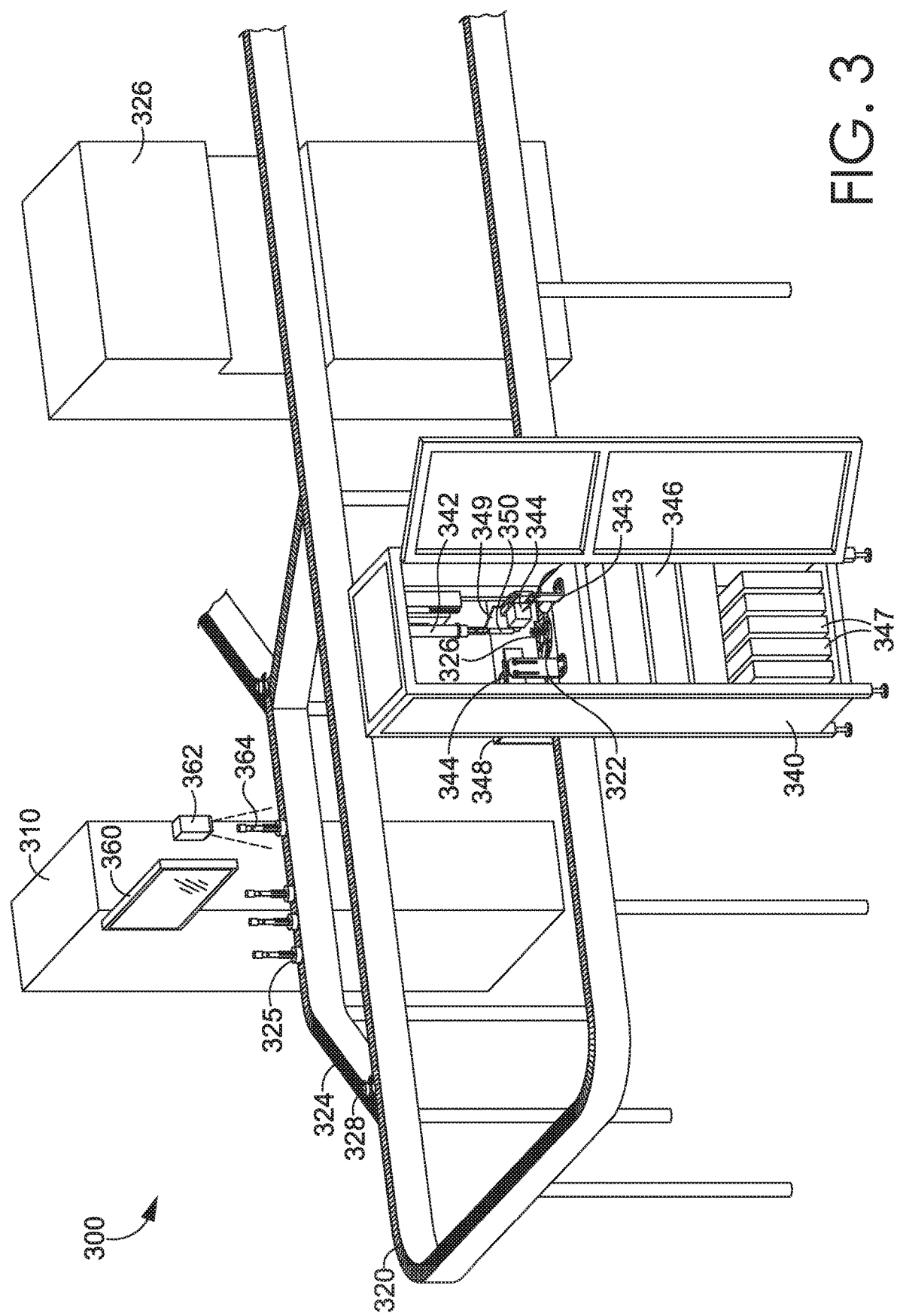
FIG. 3 is a perspective view of an automated blood sample processing apparatus suitable to implement embodiments of the system illustrated in FIG. 2, and other aspects of the present invention.

As shown in FIG. 3, in one embodiment, an automated blood sample processing apparatus 300 having a pre-analytic SIM is provided. The apparatus 300 may comprise an automated system control ("ASC") unit 310. The ASC unit may include the automated system control 212, as described in detail with reference to FIG. 2, for controlling routing parameters associated with a sample. For example, the ASC unit 310 may route the sample to a specimen integrity monitoring ("SIM") device 340 for pre-analysis. In some aspects, the ASC unit 310 may route the sample to an error spur 324 or error lane when a defect has been detected in the sample. Further, in some aspects, the ASC unit 310 routes the sample for full processing of ordered tests associated with the sample when a defect is not detected for the sample. Additionally, the ASC unit 310 may be configured to track sample information, such as an identifier of the sample and defects/errors associated with the sample.

In some aspects, the automated blood sample processing apparatus 300 is a total lab automation system that may process a sample from beginning to end without user intervention, other than sample determined to be defective. The apparatus 300 may include one or more sample routing tracks, e.g. 320 and 324, for moving samples throughout the apparatus 300. In some aspects, the automated blood sample processing apparatus 300 includes a main track 320 for routing the sample through the entire processing system. Additionally, in aspects herein, the automated blood sample processing apparatus 300 has one or more spurs off the main track 320. In one aspect, the apparatus 300 includes a SIM spur. The sample may be routed to the SIM spur based on the routing parameters in ASC unit 310 associated with the sample. In another aspect, the SIM device 340 may be mounted directly to the main track 320.

In one aspect, the automated blood sample processing apparatus 300 may include the SIM device 340 for determining one or more properties of the sample. Accordingly, a sample may be routed to the SIM device 340, based on routing parameters associated with the sample. SIM device 340 may comprise a sample extraction device 342 for extracting the sample from a sample holder for analysis. Sample extraction device 342 may also rotate the sample for capturing sensor information for analyzing a sample. In some aspects, the sample extraction device 342 may be configured to rotate the sample 360° in order to capture a plurality of images of the sample. Additionally, the sample extraction device 342 may return the sample to the sample holder when the sensor information has been captured.

The SIM device 340 may include and employ one or more sensors 344 to capture sensor information and a sample properties processor 230 (described above with reference to FIG. 2) to determine one or more properties of the sample. In one aspect, the one or more sensors 344 are configured to capture a plurality of images of the sample. Additionally, the one or more sensors 344 may capture sensor information including a plurality of color elements for the sample. Further, the one or more sensors 344 may comprise a red color detector, a blue color detector, and a green color detector, for detecting the plurality of color elements for the sample. In some aspects, the one or more sensors 344 include a black and white camera for capturing barcode information on the sample. In additional aspects, the one or more sensors 344 comprise a sample tube width detector; and a contour alignment detector for measuring a tilt angle of the sample and aligning the one or more sensors 344. The sample tube width detector may determine a width of a sample tube to determine a type of sample being processed. The contour alignment detector may operate to sense that a sample is off-center, or not exactly vertically oriented, and communicate an orientation of the sample to the other sensors.

The SIM device 340 may also include a SIM control unit 346 that includes a variety of computing and communications devices. The SIM control unit 346 may include a communications hub 347, which facilitates this communication between the SIM device 340 and other components and devices, such as ASC unit 310. The sample properties processor 230 may determine based on the plurality of images, a cap color and a liquid volume of the sample.

Further, in some aspects, the sample properties processor 230 receives the plurality of color elements and generates one or more color arrays for the sample. The sample properties processor 230 may also determine, based on the one or more color arrays and the liquid volume of the sample, a presence of one or more defects in the sample. Additionally, upon determining a presence of the one or more defects, the sample properties processor 230 may communicate an indication of the one or more defects to the ASC unit 310. Further, in some aspects, the sample properties processor 230 creates a digital record of the barcode information sensed by the one or more sensors 344 and communicates the digital record of the barcode information to the ASC unit 310 for tracking information associated with the sample.

As mentioned above, the sample routing track may include an error spur 324 for diverting the sample from the main track 320. The ASC unit 310 may be configured to direct the sample to the error spur 324 based on the indication of the one or more defects. The error spur 324 may generally operate to hold the sample for manual handling by a technologist. The sample routing track may also include one or more routing gates for transferring samples to and from the various tracks and spurs of the apparatus 300. For example, the sample routing track may include: a first electronically-actuated routing gate 322 for routing the sample from the main track 320 to the SIM device 340; a second electronically-actuated routing gate for routing the sample through the integrity monitor spur and returning the sample to the main track 320; and a third electronically-actuated routing gate 328 for routing the sample from the main track 320 to the error spur 324. The one or more routing gates may be electronically actuated, pneumatically actuated, or actuated using any other suitable means.

Figure 4:
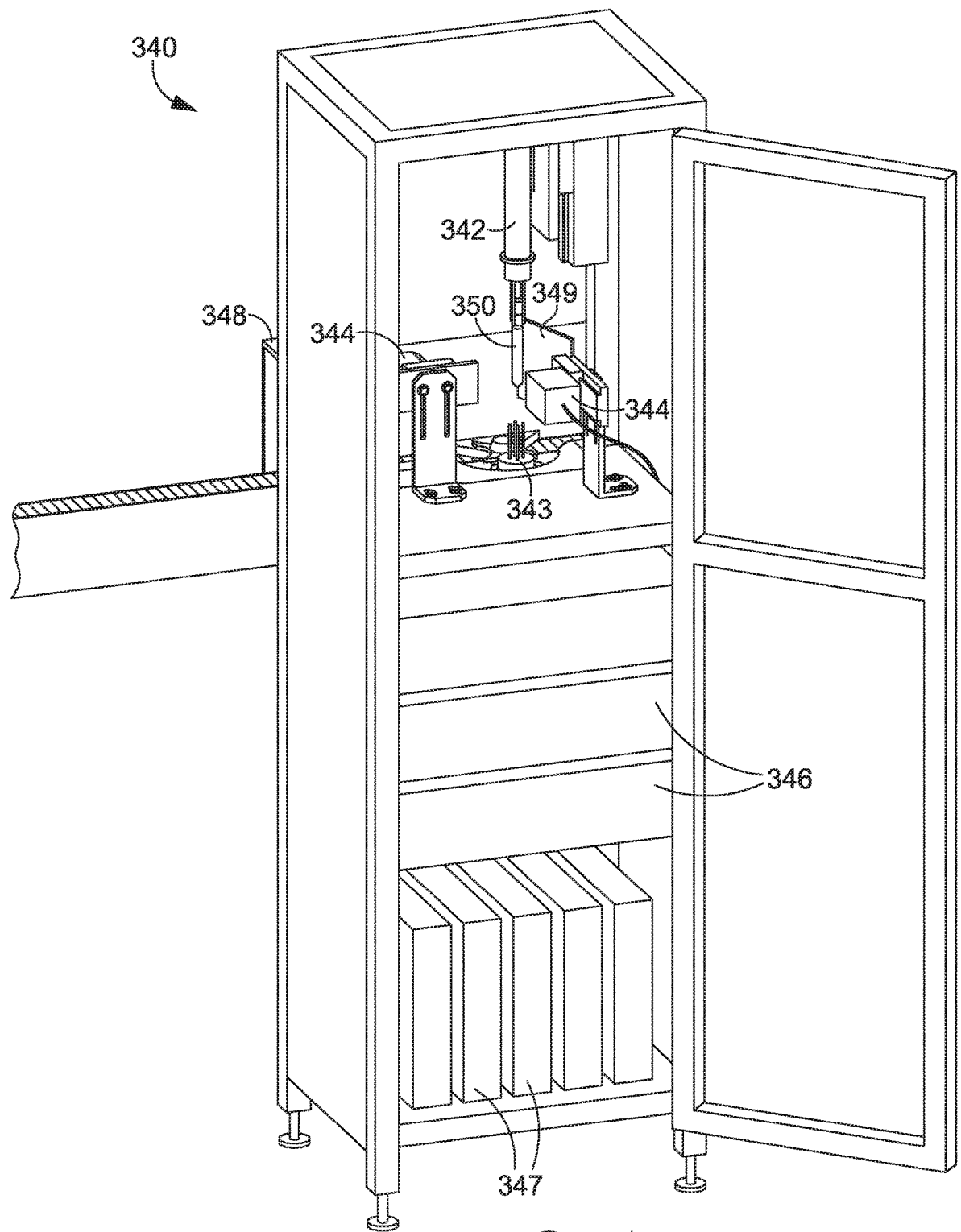
FIG. 4 is a perspective view of a specimen integrity monitoring device suitable to implement embodiments of the system illustrated in FIG. 2, and other aspects of the present invention.

Turning now to FIG. 4, in another embodiment, a pre-analytic SIM device 340 for detecting one or more defects associated with blood samples is provided. The device may comprise one or more sensors 344, for capturing a plurality of images of a sample. The one or more sensors 344 may include, for example, a red color detector, a blue color detector, and a green color detector, for detecting a plurality of color elements for the sample. In some aspects, the one or more sensors 344 include a contour alignment detector for measuring a tilt angle of the sample and aligning the one or more sensors 344. Further, in some aspects, the one or more sensors 344 comprise a sample tube width detector. Additionally, as discussed above, the one or more sensors 344 may include a black and white camera for capturing barcode information on the sample.

In some aspects, the SIM device 340 includes a SIM control unit 346 having a sample properties processor 230 that receives the plurality of color elements and generates one or more color arrays. The sample properties processor 230 may determine based on the plurality of images of the sample, a cap color and a liquid volume of the sample. In some aspects, the sample properties processor 230 determines, based on the one or more color arrays and the liquid volume of the sample, if one or more defects are present in the sample. Additionally, in aspects herein, the presence of the one or more defects is determined when at least one color array of the one or more color arrays or the liquid volume of the sample is outside of a predefined volume range for the sample. In one aspect, the one or the defects determined by the a sample properties processor 230 comprise one or more of: a sample volume defect; a hematocrit defect; a hemolysis defect; a clotting defect; an icterus defect; and a lipemia defect.

The SIM device 340 may also include a sample extraction device 342 for extracting the sample from a sample holder for analysis. Further, in some aspects, the sample extraction device 342 is configured to rotate the sample for capturing sensor information and to return the sample to the sample holder when the sensor information has been captured. Further, in some aspects, the SIM device 340 is configured to be mountable to a track of an existing automated blood sample processing apparatus. A sample lighting mechanism 349 for providing light while the plurality of images are captured may also be included in the SIM device 340.

In another embodiment, a pre-analytic SIM device 340 configured for integration with an existing automated blood sample processing apparatus is provided. In some aspects, the SIM device 340 for identifying a presence of one or more defects in one or more samples is provided. In additional aspects, upon identifying the presence of the one or more defects, the SIM device 340 communicates an indication of the one or more defects to the ASC unit 310.

In one aspect, the apparatus 300 includes an error spur 324 that receives one or more defective samples, the error spur 324 having a holding area for holding the one or more defective samples for manual inspection by a technologist. The apparatus may also include an ASC user interface 360 that facilitates the manual inspection. The ASC user interface 360 may be configured to present information relating to sample defects and overrides of the defects by the technologist. Additionally, the ASC user interface 360 may be configured to present one or more selectable indications of reasons corresponding to an override command.

One or more processors of the ASC unit 310 may include one or more computer storage media storing computer-useable instructions that, when used by the one or more processors, cause the one or more processors to perform operations. In one aspect, the operations comprise receiving an indication of an identity of the technologist via one or more ASC input devices 362. The indication of the identity of the technologist may be received via a scan of a badge associated with the technologist captured using the one or more ASC input devices 362. Additionally, the operations may include presenting, on the user-interface, one or more images and an identification of the one or more defects associated with one or more defective samples. Further, the one or more processors may receive an override command corresponding to a sample of the one or more defective samples. In some aspects, the operations comprise creating a digital record of the override command including the identity of the technologist, an identifier of the sample, and the indication of the one or more defects. The ASC unit 310 may be configured to, for example, upon receiving the digital record of the override command, route the sample for continued processing.

Figure 5:
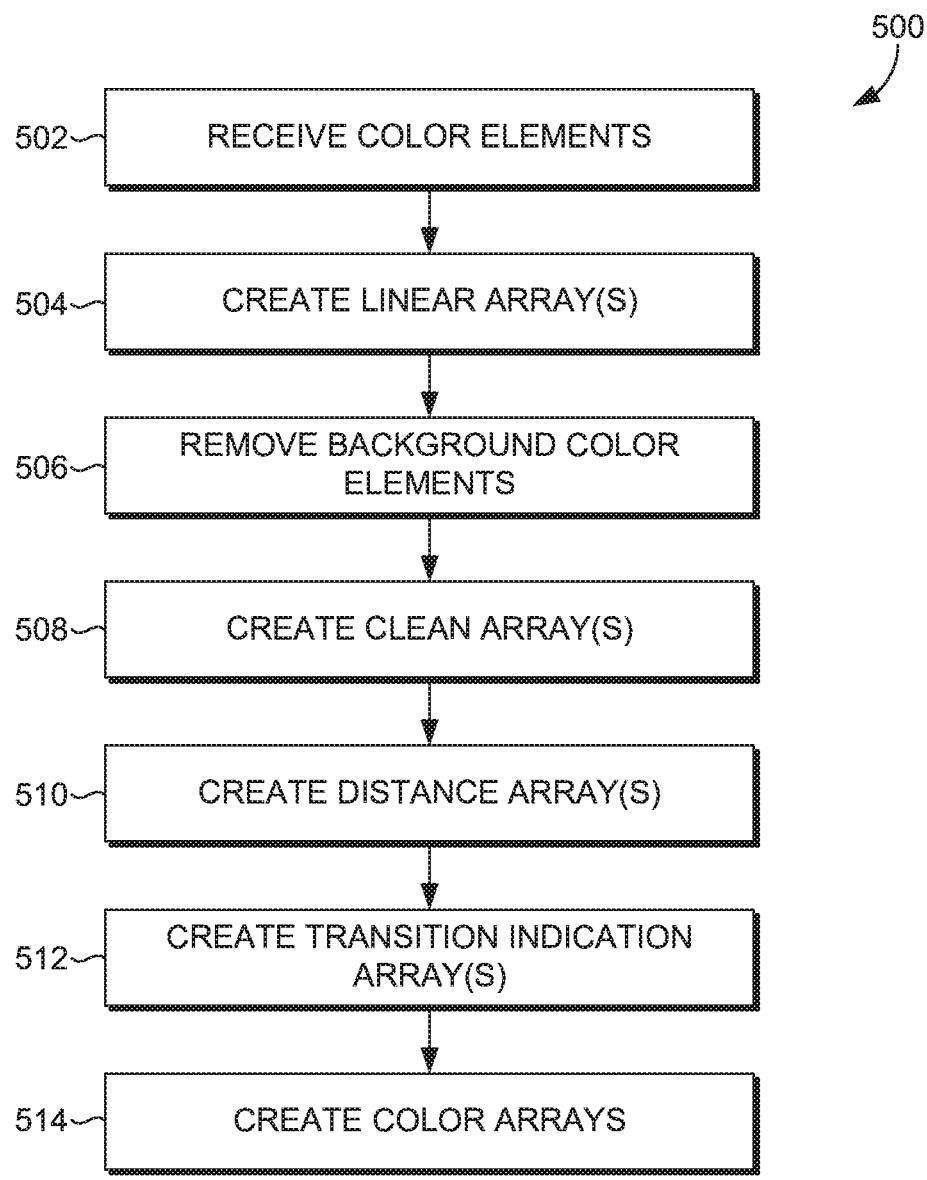
FIG. 5 is a flow diagram of a computer-implemented method for identifying blood components and properties in blood samples and reference samples in an automated blood sample processing system, in accordance with aspects herein.

Using Image Data Elements to Identify and Establish Reference Ranges for Liquid Blood Components In one embodiment, as shown in FIGS. 2 and 5, a system for identifying blood components and properties in blood samples and reference samples in an automated blood sample processing system 210 is provided. In some aspects, the system may include one or more devices storing computer-useable instructions for performing operations in the automated blood sample processing system 210. The system may comprise one or more sensors for capturing sensor data elements for one or more samples. The sensors may include, for example as discussed in more detail hereinabove, a red color detector, a blue color detector, and a green color detector, for detecting the plurality of color elements for the sample. In some aspects, the one or more sensors include a black and white camera for capturing barcode information on the sample. In additional aspects, the one or more sensors comprise a sample tube width detector; and a contour alignment detector for measuring a tilt angle of the sample and aligning the one or more sensors. The sample tube width detector may, for example, determine a width of a sample tube to determine a type of sample being processed. The contour alignment detector may operate to sense that a sample is off-center, or not exactly vertically oriented, and communicate an orientation of the sample to the other sensors.

The system may comprise a sample properties processor 230 having one or more components for identifying sample properties. In some aspects, the system includes one or more computer storage media storing computer-useable instructions that, when used by the sample properties processor 230, cause the sample properties processor 230 to perform operations. The operations may a method 500 for identifying sample properties, as shown in FIG. 5.

At block 502, in one aspect, the operations may comprise receiving, from the one or more sensors, a plurality of color elements for a sample. In some aspects, the plurality of color elements comprises one or more channel values. The channel values may include: a red channel value; a blue channel value; and a green channel value. The channel values may be communicated by the sensors as a telegram, with delimiters for separating the RB G values.

As shown at block 504, in some aspects, a linear array generator 232 may generally be configured for creating a digital record of the plurality of color elements as a linear array. The linear array generator 232 may map the color elements as a straight line, in order to determine a distance between the color elements. Accordingly, distances and linear space may be used to determine how far apart color elements are, as a proxy for identifying differences between colors.

The operations may also include creating a clean array, as illustrated at block 508. Creating the clean array may comprise determining, by a background identifier 234, one or more background color elements of the linear array. In one aspect, the one or more background color elements are outside of a predetermined range of valid color elements. In some aspects, the background elements are color elements having a brightness outside of a predetermined valid brightness range. In some aspects, the operations may include removing, by the background identifier 234, the one or more background color elements from the linear array. Additionally, in aspects herein, the operations may include creating a digital record of the remaining color elements of the plurality of color elements as a clean array.

Further, as illustrated at block 510, the operations may include creating a distance array. Creating a distance array may comprise determining, by a distance array generator 236, a distance between each color element of the clean array. Additionally, in some aspects, the operations include creating, by the distance array generator 236, a digital record of the distance between each color element as a distance array. In one aspect, as described in detail with reference to FIG. 2 above, the distance between the plurality of color elements may be determined using a Euclidean distance formula.

As shown at block 512 additionally, the operations may include creating a transition indication array. Creating the transition indication array may include, determining, by a transition indication array generator 238, if each distance of the distance array is above a transition indication threshold. In aspects herein, a distance above the transition indication threshold indicates a color transition. Further, the transition indication array generator 238 may create a digital record of the transition indication array. In additional aspects, the distance between each transition indication is compared to a transition frequency threshold to determine one or more boundary regions. Further, in some aspects, a boundary region midpoint is determined for each boundary region of the one or more boundary regions and mapped as a single color transition in the transition indication array.

In one aspect, as illustrated at block 514, a liquid portions determiner 242 may generally operate to cut (or otherwise separate) the transition indication array at each color transition to create one or more color arrays. Each color array may have a color value corresponding to a liquid blood property of the sample.

Further, in some aspects, the liquid portions determiner 242 may be configured to determine a merged color for each color array. The merged color generally represents a testable value for the blood component. The merged color may also be determined by generating a normal distribution weighted average of the one or more color elements of the color array. Additionally, a liquid portions determiner 242 may be configured for determining a number of color elements in each color array, and removing color elements beyond a color array size threshold.

Figure 6:
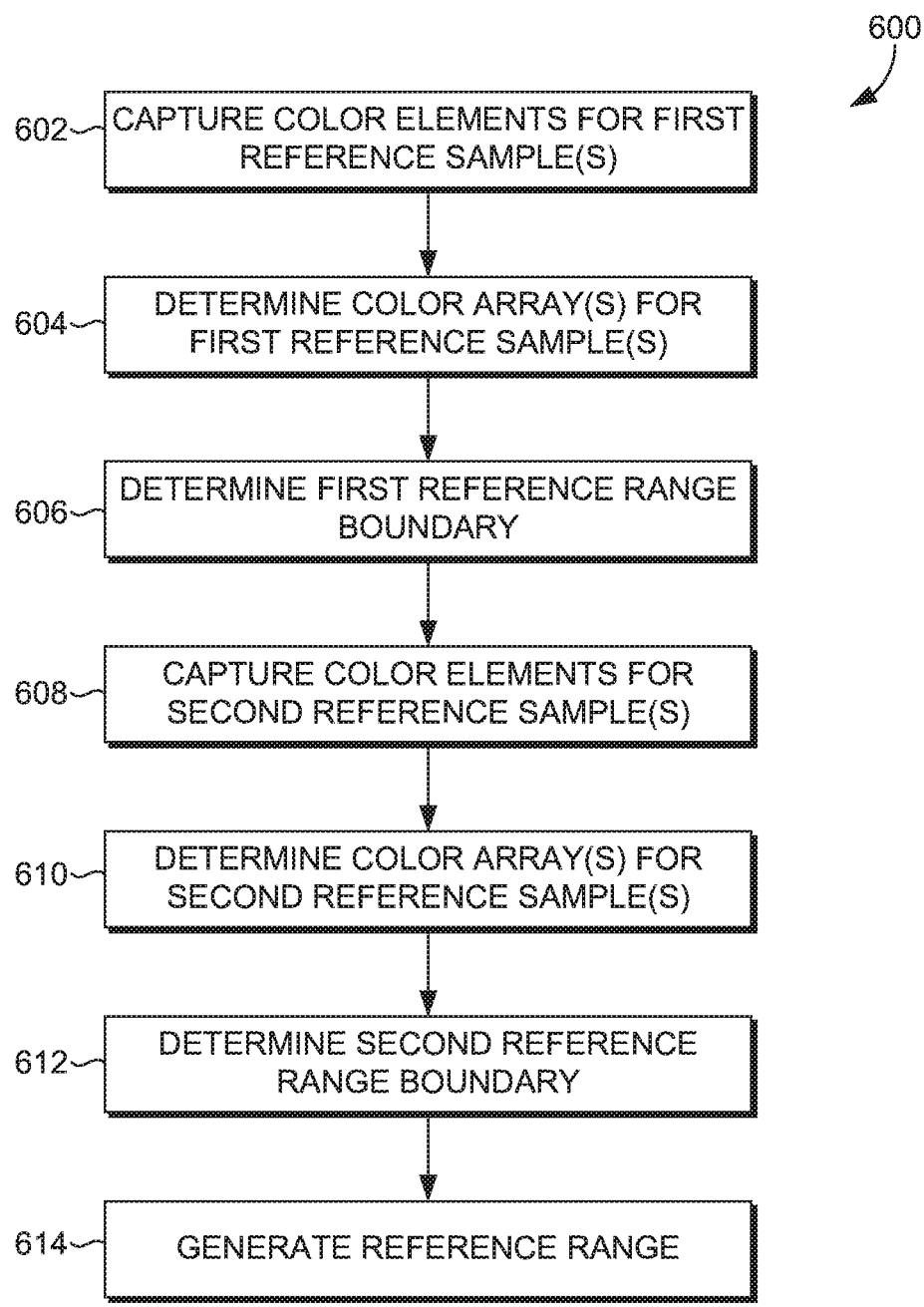
FIG. 6 is a flow diagram illustrating a computer-implemented method for setting one or more reference ranges for performing a pre-analysis of blood samples to detect specimen defects in an automated blood sample processing system, in accordance with aspects herein.

In another embodiment, as shown in FIGS. 2 and 6, a system for setting one or more reference ranges for performing a pre-analysis of blood samples to detect specimen defects in an automated blood sample processing system 210 is provided. In some aspects, the system may include one or more devices storing computer-useable instructions for performing operations in the automated blood sample processing system 210. The system may comprise one or more sensors for capturing sensor data elements for one or more samples. As described in more detail hereinabove, the system may comprise a variety of sensors. In a nonlimiting example, the sensors may include RGB detectors, a sample tube width detector, and/or a contour alignment detector.

The system may comprise a sample properties processor 230 having one or more components for identifying sample properties. In some aspects, the system includes one or more computer storage media storing computer-useable instructions that, when used by the sample properties processor 230, cause the sample properties processor 230 to perform operations. The operations may comprise a method 600 for setting one or more reference ranges for performing a pre-analysis of blood samples to detect specimen defects, as shown in FIG. 6.

As shown in FIG. 6, at block 602, the operations may comprise capturing, by one or more sensors, a plurality of color elements for a first reference sample. In aspects herein, the first reference sample corresponds to a testable criteria associated with a liquid blood component. As discussed in more detail above, the testable criteria may include one or more of: a hematocrit criteria; a hemolysis criteria; a clotting criteria; an icterus criteria; and a lipemia criteria.

As shown at block 604, in one aspect, the operations may comprise determining, by a liquid portions determiner 242, a color array for the first reference sample, the color array for the first reference sample comprising one or more color elements of the plurality of color elements for the first reference sample.

In some aspects, as shown at block 606, the operations include determining a first reference range boundary. The first reference range boundary may be determined by a reference range determiner 244, based on the color array for the first reference sample. Further, in some aspects, the operations include creating a digital record of the first reference range boundary. In some aspects, the first reference range boundary has a corresponding color value, based on the color array. Additionally, in aspects herein, the first reference sample is a sample having a predetermined minimum sample criteria value for samples analyzed in the automated blood sample processing system 210. As can be appreciated, any number of samples may be run to establish reference range boundaries. In this scenario, a mean color value, or a mean of the color arrays for a plurality of reference samples may be used as the color value for the range boundary.

As shown at block 608, in one aspect, the operations may also include capturing, by the one or more sensors, a plurality of color elements for a second reference sample. In aspects herein, the second reference sample corresponds to the testable criteria, which is the same testable criteria that is associated with the first reference sample.

Further, as shown at block 610, the operations may include determining, by the liquid portions determiner 242, a color array for the second reference sample, the color array for the second reference sample comprising one or more color elements of the plurality of color elements for the second reference sample. In one aspect, the second reference sample is a sample having a predetermined maximum sample criteria value for samples analyzed in the automated blood sample processing system 210. The operations may also include, as shown at block 612, determining, by the reference range determiner 244, based on the color array for the second reference sample, a second reference range boundary and creating a digital record of the second reference range boundary. The second reference range boundary may also have a corresponding color value.

As shown at block 614, further, in some aspects, the operations may comprise generating a reference range for the testable criteria. The reference range may be generated by the reference range determiner 244, and may comprise the first reference range boundary and the second reference range boundary. As mentioned above, the operations may also include processing a plurality of reference samples within the reference range to determine a plurality of color array value for the reference range. Further, in some aspects, the reference range determiner 244 may generate a gradient of color array values between the first reference range boundary and the second reference range boundary for assigning a color array value to the sample.

Figure 7:
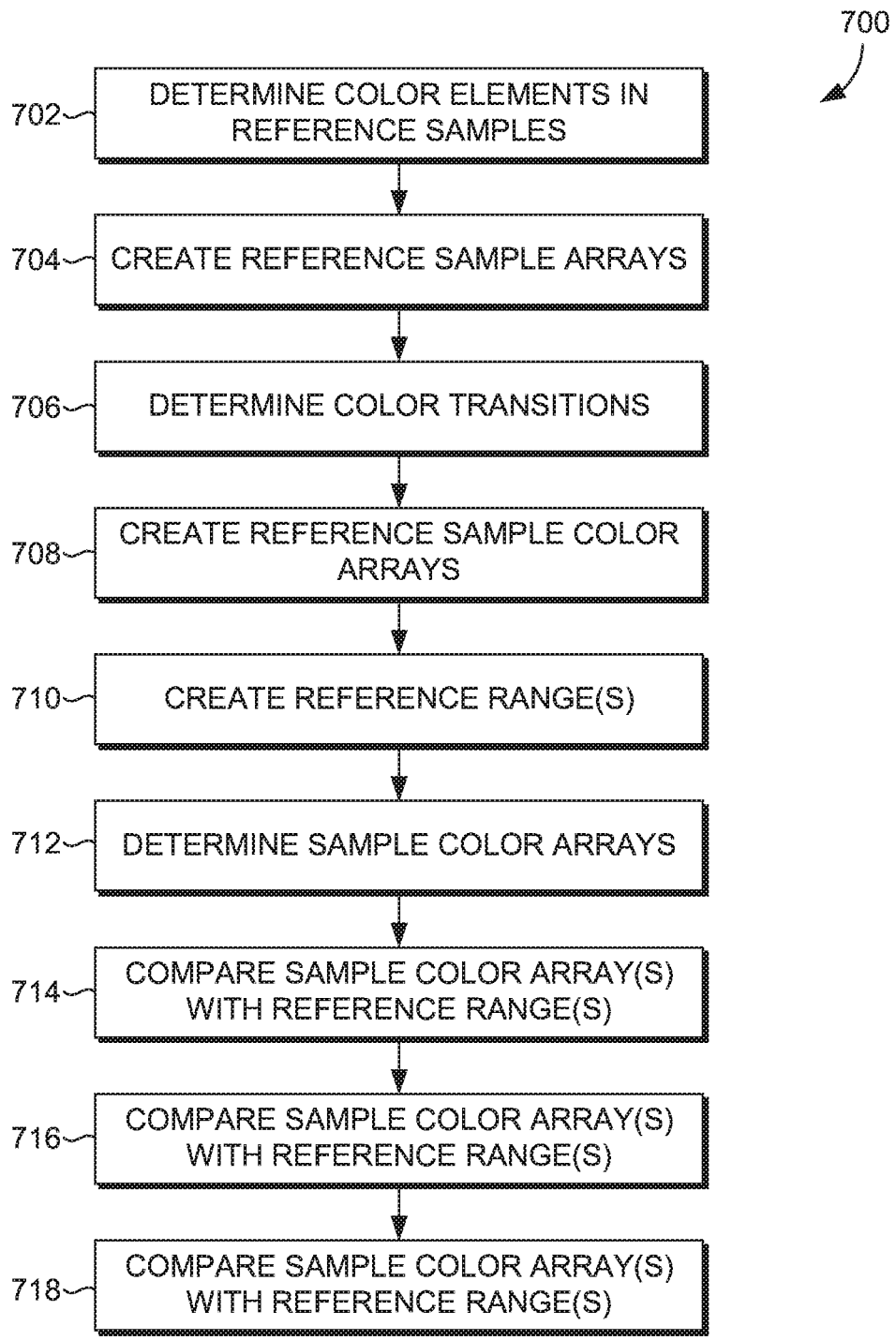
FIG. 7 is a flow diagram of a method for determining reference ranges and defects associated with blood samples in an automated blood sample processing system, in accordance with aspects herein.

Turning now to FIG. 7, an additional embodiment provides a method 700 for determining reference ranges and defects associated with blood samples in an automated blood sample processing system 210. As shown at block 702, the method may comprise determining a plurality of color elements for a first reference sample and a second reference sample. The color elements may be determined based on sensor data elements captured by one or more sensors. Additionally, the first reference sample and the second reference sample may correspond to one or more testable criteria. Additionally, the one or more testable criteria may be associated with one or more liquid blood properties. For example, the criteria may correspond to a hematocrit criteria; a hemolysis criteria; a clotting criteria; an icterus criteria; and a lipemia criteria.

As shown at block 704, in some aspects, the method comprises creating a first reference sample array and a second reference sample array, based on the plurality of color elements. In one aspect, as shown at block 706, the method comprises determining one or more color transitions for the first reference sample array and for the second reference sample array. As shown at block 708, the method may also include creating one or more color arrays for the first reference sample and one or more color arrays for the second reference sample, the one or more color arrays having color values corresponding to one or more liquid blood properties. In some aspects, the one or more color arrays are created by cutting the first reference sample array and the second reference sample array at each color transition of the one or more color transitions. As shown at block 710, the method may include creating a reference range for a testable criteria, based on the color values associated with the reference range boundaries. Further, a digital record of the reference range may be created. In one aspect, the first reference sample has a predetermined minimum testable criteria value for the reference range and the second reference sample has a predetermined maximum testable criteria value for the reference range.

In some aspects, as shown at block 712, the method comprises determining, for a sample, one or more sample color arrays. In some aspects, the one or more sample color arrays have color values corresponding to the one or more liquid blood properties. As shown at block 714, the method may comprise comparing a sample color array of the one or more sample color arrays with the reference ranges for the one or more color arrays. Additionally, as shown at block 716, the method may include determining a presence of one or more defects in the sample. The presence of the one or more defects may be determined when the sample color array is outside of the reference range for the testable criteria. As shown at block 718, in some aspects, the method includes, communicating a readable error code including an indication of the one or more defects, to an automated method control. The readable error code including the indication may be communicated, upon determining a presence of the one or more defects.

As can be appreciated, the steps of the method 700 may be accomplished or carried out in the one or more components of the system 200 described hereinabove with reference to FIG. 2. Accordingly, a system that implements the steps described in method 700 via the processors and components described hereinabove should be considered within the scope of the present disclosure.

Identifying Sample Defects

Figure 8:
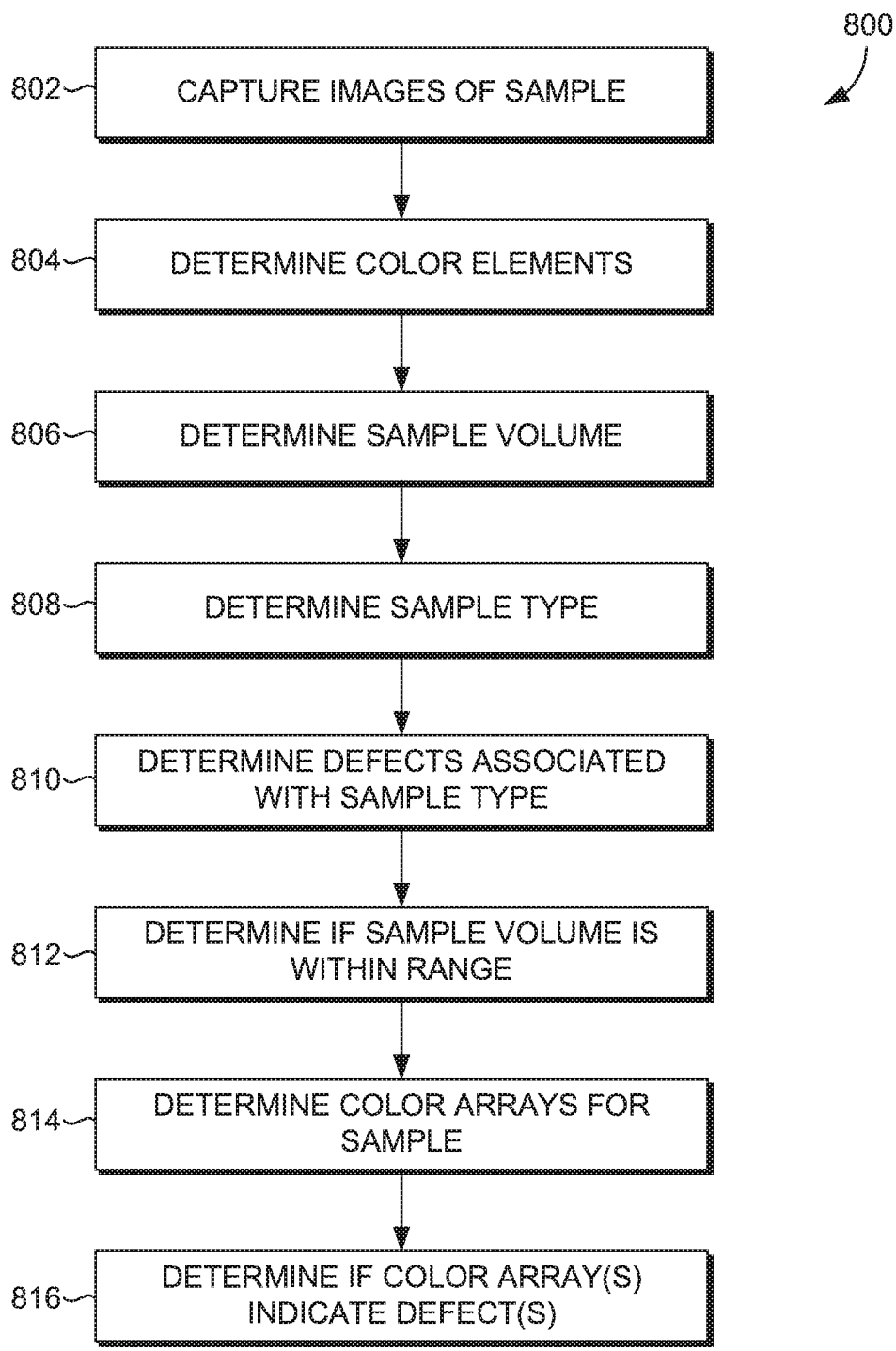
FIG. 8 is a flow diagram of a method for performing a pre-analysis of blood samples to detect specimen defects and tube properties, in accordance with aspects herein.

In one embodiment, as shown in FIG. 8, a method 800 for performing pre-analysis of blood samples to detect specimen defects and tube properties is provided. As shown at block 802, the method may comprise capturing, by one or more sensors, a plurality of images of a sample. In some aspects, as shown at block 804, the method includes determining, various properties of the sample based on the plurality of images. In one aspect, a plurality of color elements for the sample are determined, based on the images. In some aspects, as shown at block 806, a tube size and a liquid volume of the sample are also determined. Further, in some aspects, the method may include capturing barcode information from a barcode on the sample. Additionally, in some aspects, the sample properties processor 230 creates a digital record of the barcode information and communicates the digital record of the barcode information to an ASC 212 for tracking sample information.

As shown at block 808, in some aspects, the method includes determining, based on the plurality of color elements, a cap color of the sample. Additionally, in some aspects, the method includes determining a sample type corresponding to the cap color. A given color may be associated with a specific type of sample. Associations between cap colors and sample types may be stored in, for example, the ASC 212. Additionally, the associations may be communicated to and stored by the sample properties processor 230. Additionally, in aspects herein, a complete image of the sample and a digital record of the complete image may be created, based on the plurality of images. Further, in some aspects, the method comprises communicating the digital record to the ASC 212.

In one aspect, as shown at block 810, the method includes determining, based on the sample type, one or more defects to be analyzed for the sample type. For example, a light blue tube cap may be associated with a hematocrit sample type. Continuing with this example, because the sample type is a hematocrit sample type, it may be determined that only defects that cause interference with a hematocrit sample need to be determined. In some aspects, the one or more defects may include one or more of: a volume defect; a hematocrit defect; a hemolysis defect; a clotting defect; an icterus defect; and a lipemia defect.

As shown at block 812, the method may include determining if the liquid volume of the sample outside of a predefined volume range associated with the sample type. Just as sample types may have associated defects, each sample type may also require a minimum volume to perform a valid test. Accordingly, a minimum volume for each sample type may be predetermined and stored for comparison to samples. As a result, method may further include rejecting the sample when the liquid volume is below a minimum volume associated with the predefined volume range.

The method may also include, as shown at block 814, determining, one or more color arrays for the sample. The color arrays may be determined based on the plurality of color elements, as described hereinabove. Further, each color array may correspond to a defect of the one or more defects. Lastly, as shown at block 816, the method may include determining if the each color array is outside of a reference range for a corresponding defect. As can be appreciated, when a color array is outside of the reference range, a defect may be indicated. Accordingly, the method may also comprise rejecting the sample when one or more color arrays is outside a reference range for a corresponding defect.

Figure 9:
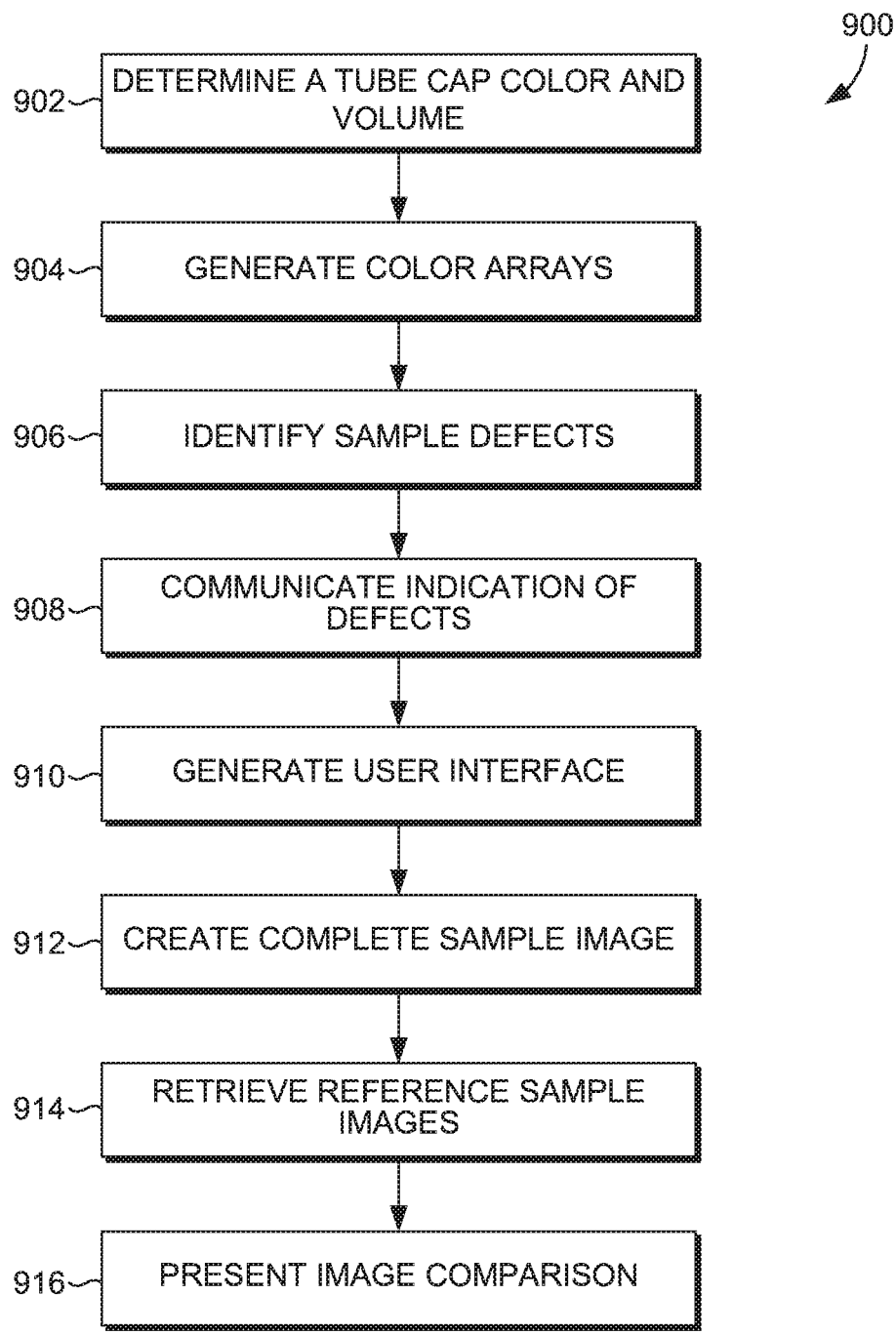
FIG. 9 is a flow diagram of a computer-implemented method for determining properties associated with a blood sample in an automated blood sample processing system, in accordance with aspects herein.

In another embodiment, as shown in FIGS. 2 and 9, a system for determining properties associated with a blood sample in an automated blood sample processing system 210 is provided. In some aspects, the system may include one or more devices storing computer-useable instructions for performing operations in the automated blood sample processing system 210. The system may comprise a sample properties processor 230. In some aspects, one or more computer storage media storing computer-useable instructions that, when used by the sample properties processor 230, cause the sample properties processor 230 to perform operations, as illustrated in FIG. 9. As can be appreciated, the operations may comprise a method 900 for determining sample properties.

In some aspects, as shown at block 902, the operations include determining, by a sample tube features determiner 246, a tube cap color, and a liquid volume of the sample. In some aspects, the tube cap color and the liquid volume may be determined based on the one or more images. Further, in one aspect, a plurality of color elements for the sample may be determined from the one or more images to determine the tube cap color and the liquid volume of the sample, as described hereinabove with reference to FIG. 2. In one aspect, determining the liquid volume of the sample may include identifying, based on the one or more images, one or more of: a gel barrier; an anticoagulant; and a serum. In some aspects, the liquid volume of the sample comprises a volume of liquid blood above the gel barrier, the anticoagulant; and/or the serum.

As illustrated at block 904, in one aspect, the operations include generating, by a liquid portions determiner 242, one or more color arrays. As described hereinabove for FIG. 2, the one or more color arrays may correspond to liquid portions of the blood sample associated with sample defects and/or interference. Additionally, as shown at block 906, the operations may include identifying, by a defect identifier 248, based on the one or more color arrays and the liquid volume of the sample, a presence of one or more defects in the sample.

As illustrated at block 908, in some aspects, the defect identifier 248 may communicate a readable error code including an indication of the one or more defects, to an ASC 212. As can be appreciated, the readable error code including the indication may be communicated upon identifying the presence of the one or more defect. In additional aspects, a digital record of the readable error code and an identification of the sample may be created and communicated to facilitate tracking and routing of the sample.

Further, as shown at block 910, the automated system control may generate a user interface for a manual inspection of the sample. As illustrated at block 912, the automated system control may also create a complete image of the sample, based on the one or more images. Additionally, as illustrated at block 914, the automated system control may retrieve one or more reference sample images. In some aspects, the one or more reference sample images comprise one or more images of one or more reference samples corresponding to the one or more defects. Said another way, the reference sample images may be images of reference samples for the defect identified in the sample.

As shown at block 916, generating and presenting an image comparison screen for comparing the complete image of the sample to the one or more reference sample images. In some aspects, the method may include retrieving, by the one or more processors, one or more additional complete images associated with one or more additional samples. Additionally, in one aspect, the user interface includes a sample search feature for retrieving sample data elements based on one or more of an accession number associated with a processed sample or a defect associated with the processed sample. Further, the user interface may be presented on a touchscreen interface that facilitates navigation of the user interface using a plurality of touch gestures. For example, a user may zoom-in on a portion of a sample for a reference sample image. Further, the user interface may display one or more color values associated with the sample, the one or more additional samples, or the one or more reference sample images on the image comparison screen.

Configuring SIM Reference Ranges and Compiling SIM Results

Figure 10:
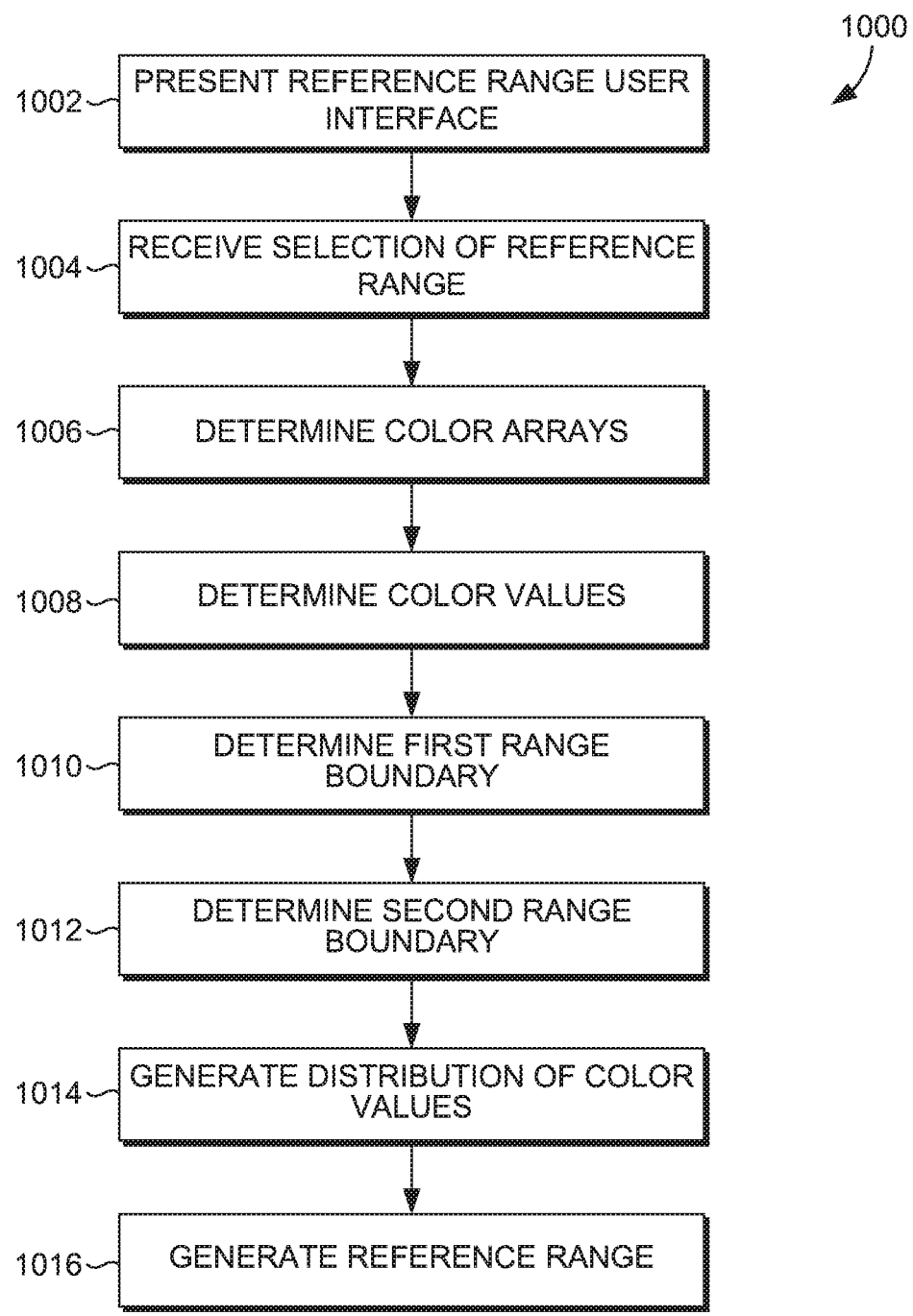
FIG. 10 is a flow diagram of a method for configuring reference range settings for a specimen integrity monitor in an automated blood sample processing system, in accordance with aspects herein.

One embodiment herein, as shown in FIG. 10, comprises a method 1000 for configuring reference range settings for a specimen integrity monitor in an automated blood sample processing system. As illustrated at block 1002, the method may comprise generating and presenting a user interface for creating one or more reference ranges for one or more testable criteria. Further, as shown at block 1004, the method may include receiving, via the user interface, a selection of a reference range of the one or more reference ranges.

As illustrated at block 1006, the method may comprise determining, for a plurality of reference samples corresponding to the selected reference range, one or more color arrays. As illustrated at block 1008, the method may include determining one or more color values corresponding to the one or more color arrays. In some aspects, the one or more color arrays are determined based on a plurality of color elements for each reference sample of the plurality of reference samples captured by one or more sensors.

As illustrated at block 1010, the method may also comprise determining a first reference range boundary, the first reference range boundary corresponding to a first color value of the one or more color values. Accordingly, as shown at block 1012 the method may include determining a second reference range boundary, the second reference range boundary corresponding to a second color value of the one or more color values. In some aspects, the first color value corresponds to a minimum color value for the testable criteria. In one aspect, the second color value corresponds to a maximum color value for the testable criteria.

As illustrated at block 1014, the method may include generating a distribution of the one or more color values between the first reference range boundary and the second reference range boundary. In some aspects, the distribution comprises one or more color values between the minimum color value and the maximum color value. Additionally, as shown at block 1016, the method may also include generating a reference range for a testable criteria, the reference range comprising the first reference range boundary, the second reference range boundary, and the distribution.

Figure 11:
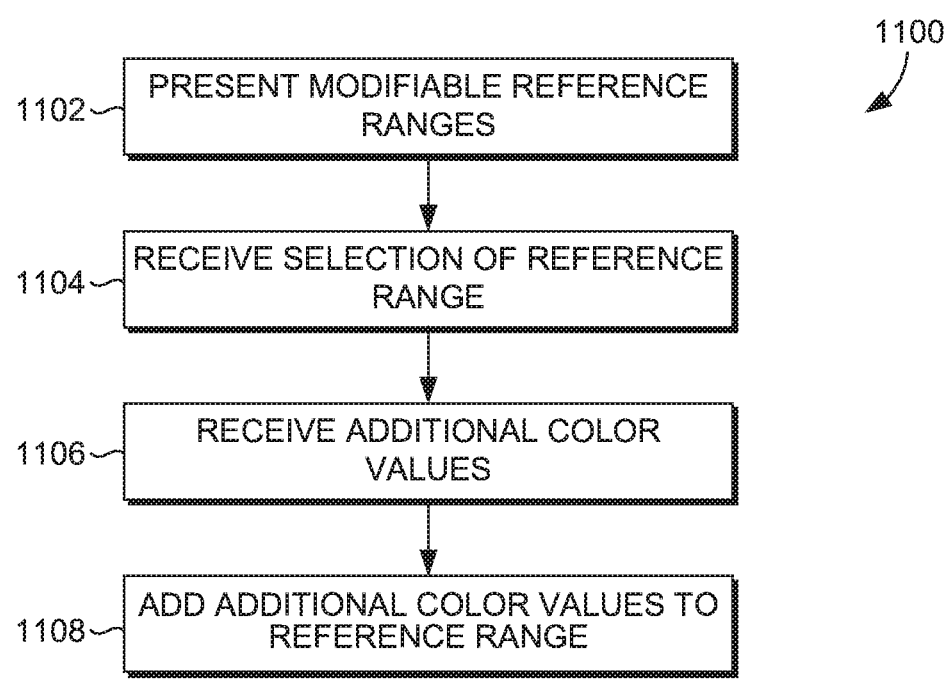
FIG. 11 is a flow diagram of a method for modifying one or more existing reference ranges for a testable criteria in an automated blood testing system, in accordance with aspects herein.

Another embodiment herein provides a method 1100 for modifying one or more existing reference ranges for a testable criteria in an automated blood testing system, as illustrated in FIG. 11. As illustrated at block 1102, the method may comprise presenting one or more modifiable reference ranges, the one or more modifiable reference ranges having a plurality of existing color values. Further, as shown at block 1104, the method may include receiving a user selection of a modifiable reference range of the one or more modifiable reference ranges. As illustrated at block 1106, the method may comprise receiving one or more additional color values for one or more additional reference samples.

Additionally, as shown at block 1108, the method may also include adding the one or more additional color values to the selected modifiable reference range. Adding the one or more additional color values to the selected reference range may include determining a first reference range boundary, the first reference range boundary corresponding to a first color value of the one or more additional color values and the plurality of existing color values. Accordingly, adding the additional color values may also comprise determining a second reference range boundary, the second reference range boundary corresponding to a second color value of the one or more additional color values and the plurality of existing color values. As can be appreciated, a distribution of the one or more additional color values and the plurality of existing color values between the first reference range boundaries may also be generated. Further, adding the one or more additional color values may include generating an updated reference range for a testable criteria, the reference range comprising the first reference range boundary, the second reference range boundary, and creating a digital record of the updated reference range.

Figure 12:
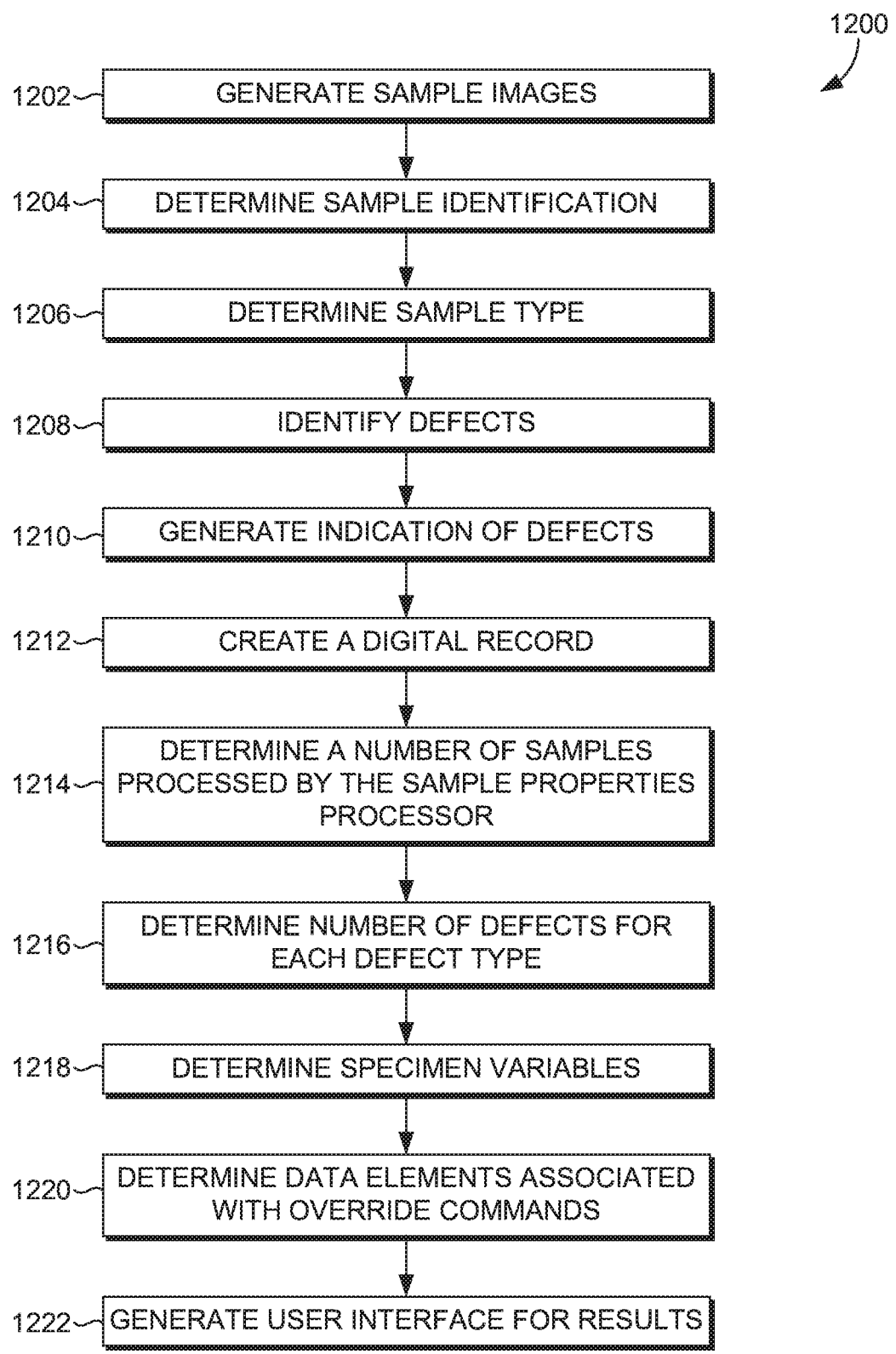
FIG. 12 is a flow diagram of a computer-implemented method for compiling results from a specimen integrity monitor in an automated blood sample processing system, in accordance with aspects herein.

Turning now to FIG. 12, an additional embodiment provides a system for compiling results from a specimen integrity monitor in an automated blood sample processing system. In some aspects, the system may include one or more devices storing computer-useable instructions for performing operations in the automated blood sample processing system 210. As can be appreciated, the operations carried out by the system may comprise a method 1200. The system may comprise one or more sensors configured to provide sensor data for a plurality of samples. In some aspects, the system includes a sample properties processor 230 for performing, based on the sensor data for each sample of the plurality of samples, operations for determining one or more data elements associated with each sample. The operations described with respect to block 1202-1212 will be addressed briefly, as each operation has been described in detail hereinabove.

The operations may include, as shown at block 1202, generating one or more images of the sample. Further, as shown at block 1204, the operations may comprise determining an identification of the sample. As illustrated at block 1206, the operations include determining a sample type for the sample. As illustrated at block 1208, a presence of one or more defects in the sample may be identified. In some aspects, as shown at block 1212, the operations include generating a readable error code including an indication of the one or more defects. As illustrated at block 1212, the operations may also include creating a digital record of the one or more data elements.

Additionally, the system may include an ASC 212 having one or more processors for generating SIM results. Further, the system may comprise one or more computer storage media storing computer-useable instructions that, when used by the one or more processors, cause the one or more processors to perform operations.

In some aspects, the operations comprise determining, by a system results compiler 220, a number of samples processed by the sample properties processor 230, as shown at block 1214. As can be appreciated, this may be accomplished in a number of ways. In one aspect, the sample properties processor 230 may store and/or communicate indications of each sample processed. For example, a sample properties processor 230 may have access to a local storage device, and may communicate a number of samples processed to the ASC 212, or to a laboratory information system 112 or healthcare information system 110, via network 106. Accordingly, the system results compiler 220 may access the stored information for processed samples in order to compile results.

Further, as shown at block 1216, the operations may include determining, by the system results compiler 220, a number of defects identified for each defect of the one or more defects. In some aspects, the defects comprise one or more of: a volume defect; a hematocrit defect; a hemolysis defect; a clotting defect; an icterus defect; and a lipemia defect. Using means similar to those described immediately above, the system results compiler 220 may access data elements, stored indications, complete sample images, color values, and any number of other information associated with samples identified as defective.

As illustrated at block 1218, the operations may include determining, by the system results compiler 220, one or more specimen variables for each sample of the plurality of samples. The one or more specimen variables may be determined, in one aspect, based on the identification of the sample. In some aspects, the one or more specimen variables comprise one or more of: a collection location; an identification a phlebotomist associated with the sample; sample handling information; and sample processing information.

In one aspect, as shown at block 1220, the operations include determining, by the system results compiler 220, a plurality of data elements associated with one or more override commands. In some aspects, the plurality of data elements associated with one or more override commands comprise one or more of: a number of override commands; one or more defects associated with the one or more override commands; a technologist associated with the one or more override commands; and one or more reasons corresponding to the override command. In some aspects, the system results compiler 220 may access override command data stored in the ASC 212, or other suitable locations within the operating environment and computing systems described hereinabove with reference to FIGS. 1 and 2.

For example, when a defect is detected in a sample, the sample may be held for manual review by a technologist. In some aspects, the technologist must scan a badge or identification card using input device or the user interface 216. Further, as a technologist performs their review of samples, the identifications of the samples may automatically be associated with the technician. Accordingly, when a given technician overrides the sample properties processor's 230 determination that a sample is defective and routes the sample for continued processing, the override automatically be associated with the technician and the sample. Further, in some aspects, when an override command is received, the plurality of sample images, color values, color arrays, specimen variables, and any other information associated with the sample, may be flagged and stored with an indication that the sample was associated with an override. By compiling sample results, particularly for samples associated with overrides, the overall system may be improved. This is so, in one aspect, because tracking overrides essentially provides an ongoing mechanism for quality control regarding determinations made by the SIM 214 and the sample properties processor 230.

Additionally, as shown at block 1222, the operations may include generating, by the ASC 212, a user interface 216 for interacting with the SIM results. In some aspects, the plurality of data elements associated with one or more override commands comprise one or more of: a number of override commands; one or more defects associated with the one or more override commands; a technologist associated with the one or more override commands; and one or more reasons corresponding to the override command. In some aspects, the SIM results comprise one or more statistics, including one or more of: a number of samples processed during a customizable time period; a number defects for each type of defect identified during the customizable time period; a number of each type of defect that originated from one or more collection locations; and a number of each type of defect associated with a particular phlebotomist.

Further, in some aspects, the user interface 216 generates and displays an image comparison screen for comparing the one or more images of a sample to a plurality of reference images. This can be an effective way of providing a real-time comparison of a sample with references and/or standards. For example, an image of a sample may be presented in a format that allows the technician to zoom in on the sample to obtain an optimal view of a sample color or colors. Further, in some aspects, color values associated with the color arrays and corresponding blood properties or defects may be displayed with the sample images. This may also provide another quality control opportunity. For example, if a color value associated with a sample determined to be defective is visibly incorrect from the perspective of the technologist, the technologist's override of the defect may indicate that reference ranges for the defect should be adjusted. Additionally, compiling results for override may provide an indication that one of the sensors, or other physical components associated with the system needs to be inspected.

Sample Tube Gripper and Rotation Device

Figure 13:
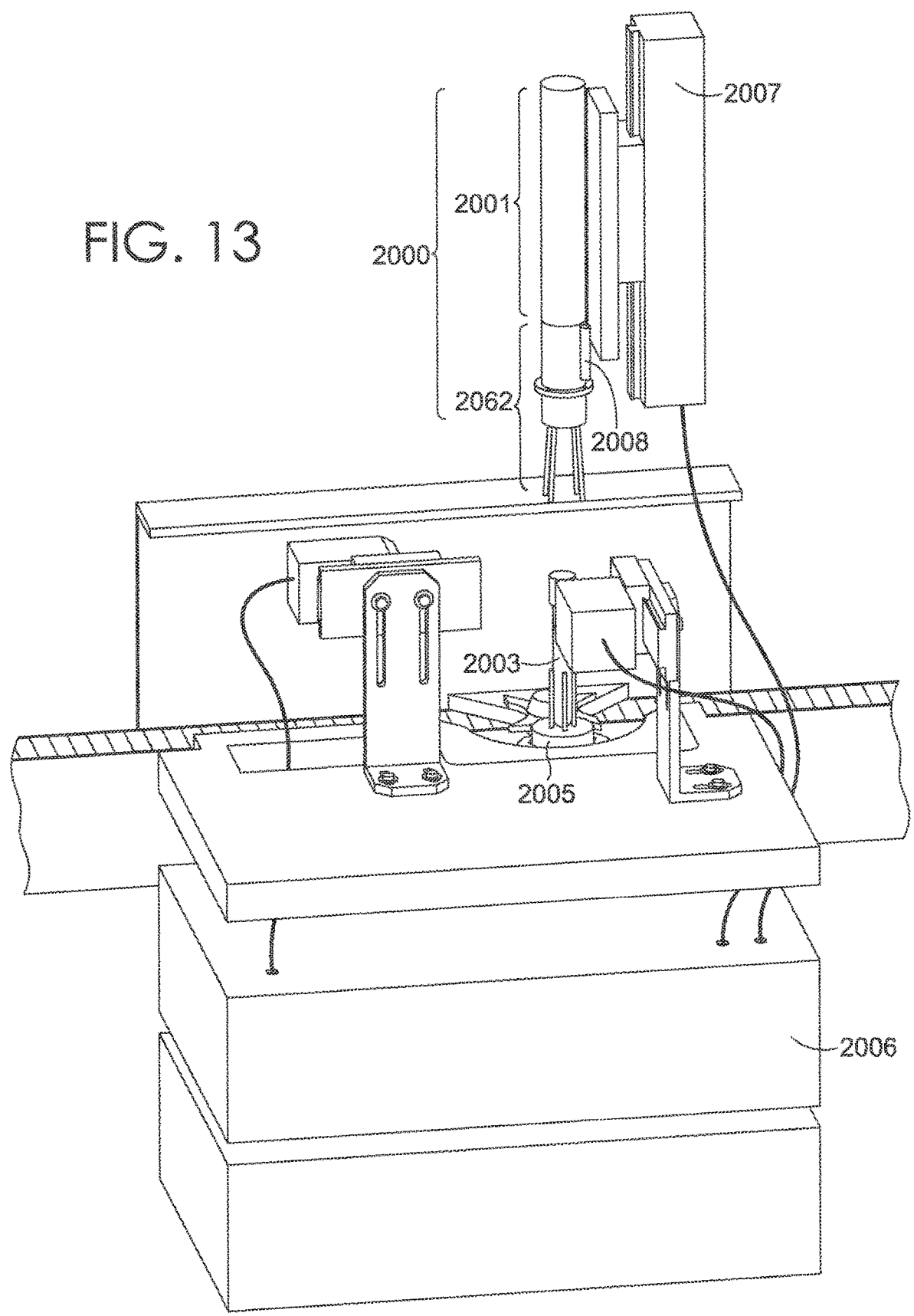
FIG. 13 is a perspective view of a sample tube gripping and rotation device, configured for use in a specimen integrity monitor, in accordance with aspects herein.

Another embodiment herein relates to a sample tube gripper and rotation device 2000, shown in FIGS. 13-17, for use in an automated blood sample processing system. Generally, the device 2000 is substantially vertically oriented, as shown in FIG. 13, such that a profile of the device 2000 corresponds to a profile of a sample tube 2003. In one aspect, the device 2000 includes a single motor 2002 for gripping a sample tube 2003 and rotating the sample tube 2003 for analysis. Because the device 2000 may employ a single motor 2002 for gripping and full rotation, a physical footprint of the device 2000 is minimized. Accordingly, the device 2000 may be well suited for use in automated blood sample processing systems, where space is often limited. For example, the device 2000 may be well suited for use in a specimen integrity monitor, as described hereinabove.

Figure 14:
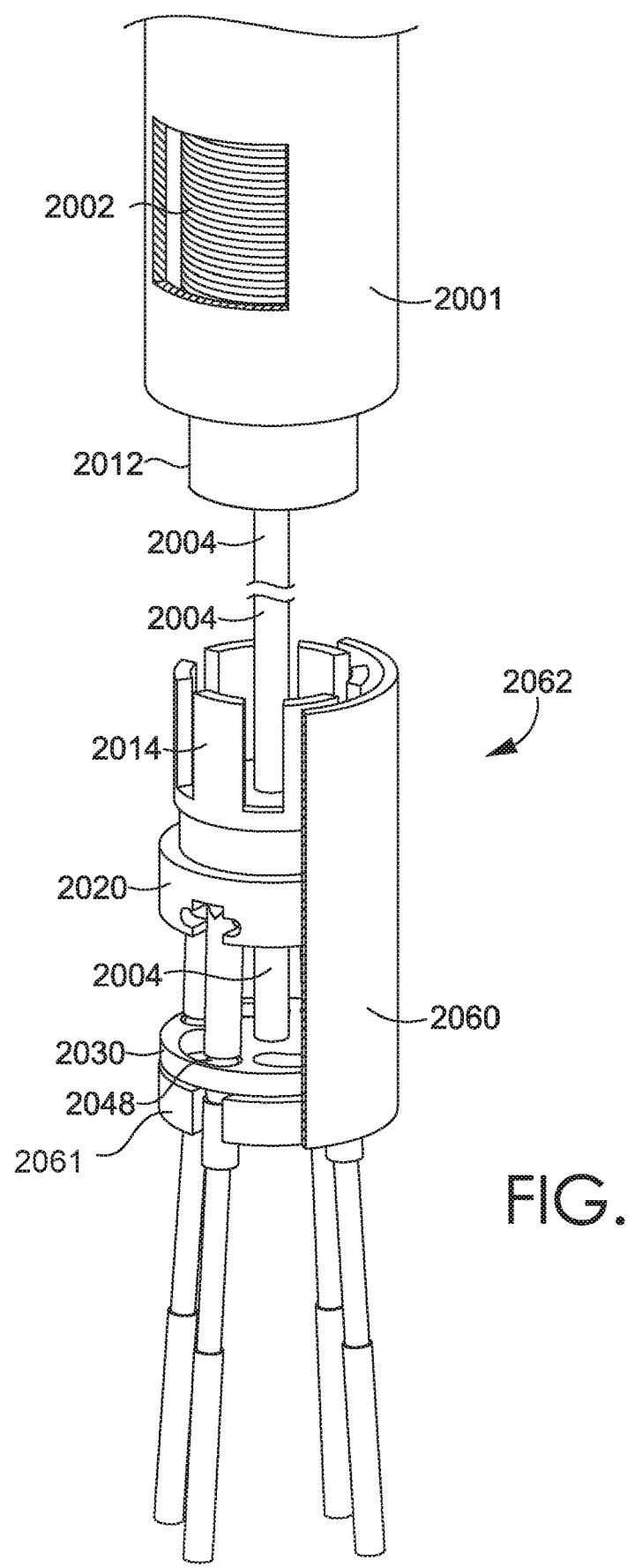
FIG. 14 is a partial cutaway, exploded-isometric, top-down perspective view of a sample tube gripping and rotation device, in accordance with aspects herein.
Figure 15:
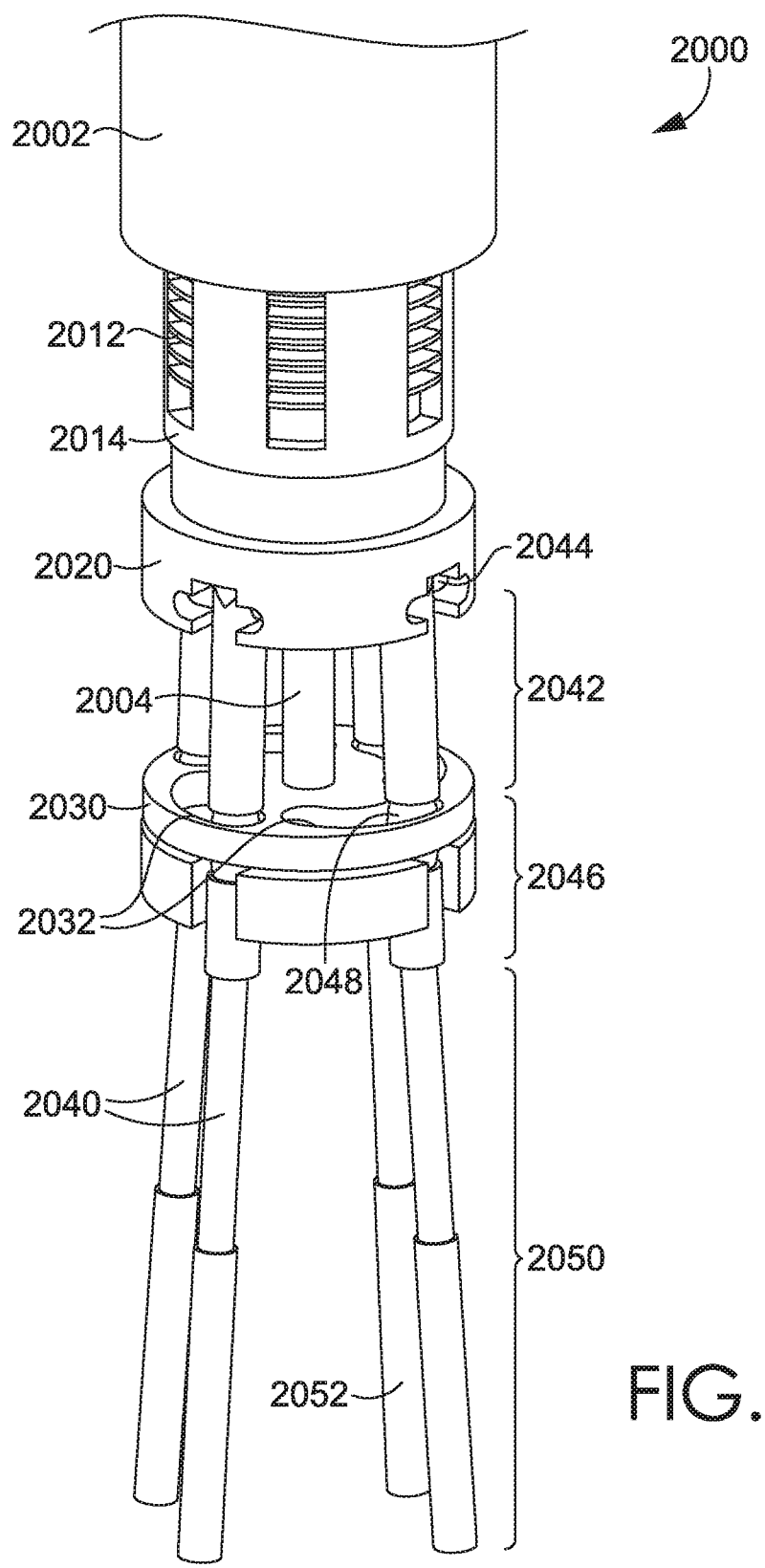
FIG. 15 is a top-down partial cutaway perspective view of the sample tube gripping and rotation device, in a first position, in accordance with aspects herein.
Figure 16:
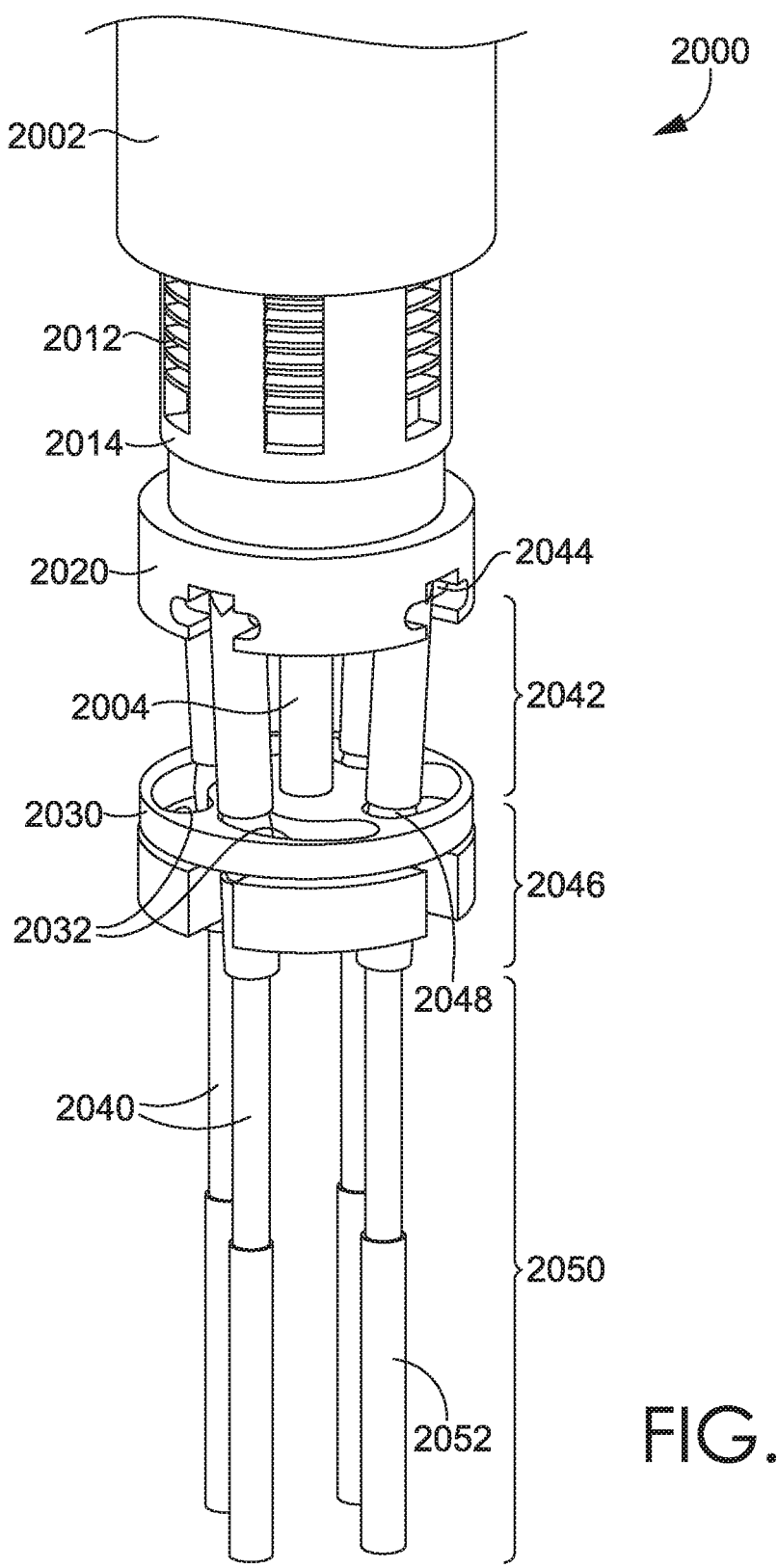
FIG. 16 is a top-down partial cutaway perspective view of the sample tube gripping and rotation device, in a second position, in accordance with aspects herein.
Figure 17:
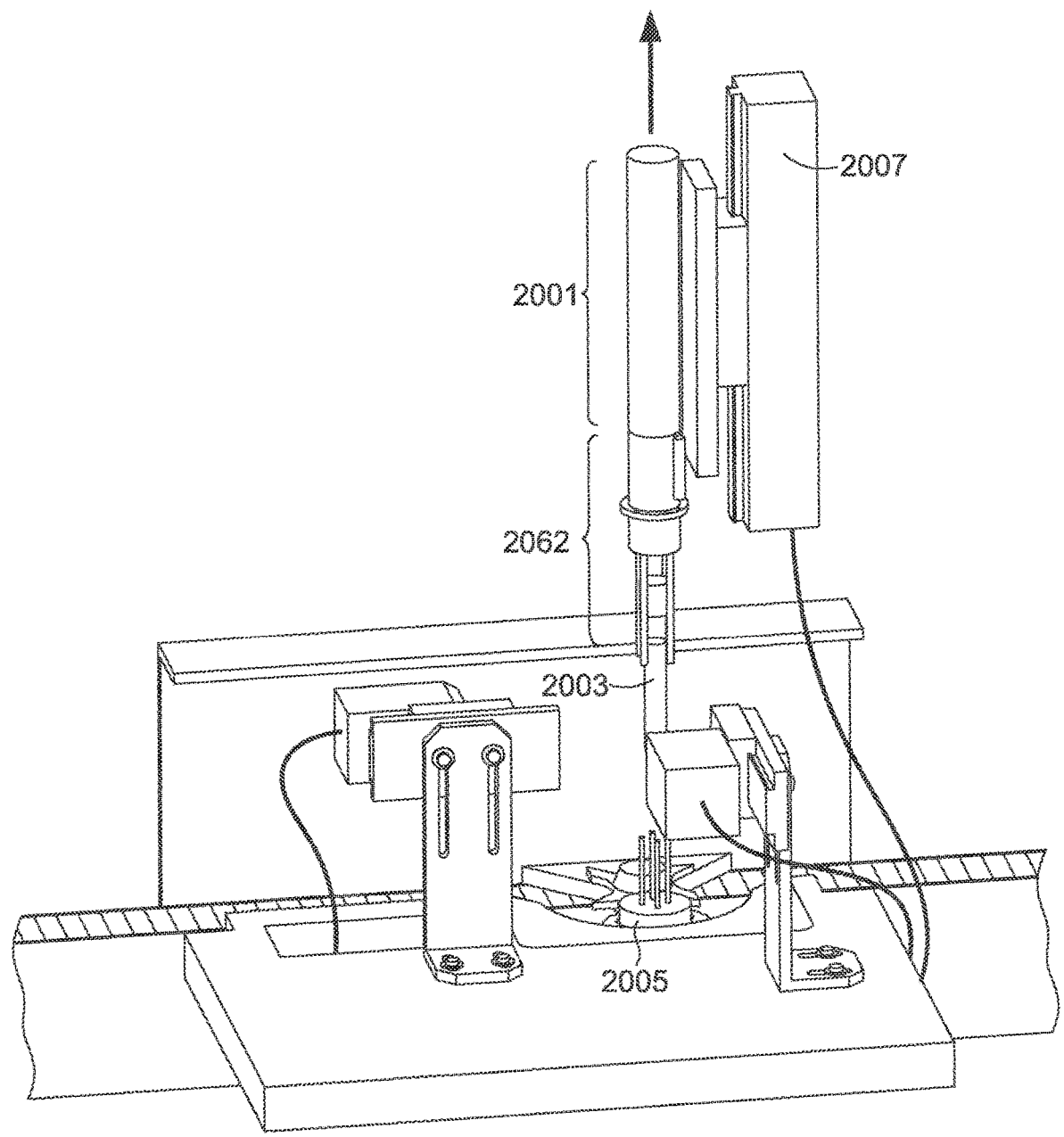
FIG. 17 is a perspective view of a sample tube gripping and rotation device, in accordance with aspects herein.

In operation, as shown in FIGS. 14-16, the device 2000 first actuates two or more fingers 2040 by imparting a first level of rotational torque to securely hold a sample tube 2003. Next, the device 2000 increases rotational torque to a level above the first level in order to overcome a slip clutch 2010. As a result, when the slip clutch 2010 has been overcome, the device 2000 may freely rotate while maintaining a secure gripping force on the sample tube 2003. Accordingly, the device 2000 may operate to grip a sample tube 2003, as shown in FIG. 17, and continually rotate the sample tube 2003 while sensor 2008 data is being acquired by the specimen integrity monitor.

Accordingly, in one embodiment, a sample tube 2003 gripping and rotation device 2000 for use in an automated blood sample processing system is provided. As illustrated in FIG. 14, the device 2000 may include a vertically-oriented motor 2002 and an upper housing 2001. The motor 2002 may be an electric motor 2002 that is configured to rotate in a forward direction and a reverse direction. In some aspects, the direction of the motor 2002 may be changed by reversing current supplied to the motor 2002. Additionally, the device 2000 may include a vertically-oriented driveshaft 2004 extending downward from the motor 2002 and through the upper housing 2001.

Further, the device 2000 may comprise a slip clutch 2010 positioned about and spaced apart from the driveshaft 2004. The slip clutch 2010 may comprise a fixed portion 2012 and a rotating portion 2014. In one aspect, the fixed portion 2012 is affixed to the upper housing 2001. In some aspects, the device 2000 may comprise a pivot housing 2020 positioned about and spaced apart from the driveshaft 2004. The rotating portion 2014 of the slip clutch 2010 may be affixed to the pivot housing 2020 such that the pivot housing 2020 is disposed below the slip clutch 2010. In additional aspects, the device 2000 may include a horizontally-oriented slotted cam 2030 disposed below the pivot housing 2020 and coupled to a distal end of the driveshaft 2004. The slotted cam 2030 may comprise two or more slots 2032 extending diagonally outward from the center of the slotted cam 2030.

In one aspect, the device 2000 may include two or more vertically-oriented fingers 2040. In one aspect, each finger 2040 includes an upper portion 2042 comprising a pivot 2044, which may be pivotably retained in the pivot housing 2020. The pivot 2044 may be retained such that movement of the fingers 2040 in axial and radial directions are eliminated, or limited. However, the pivot 2044 is configured to allow tangential movement of the fingers 2040. Additionally, the fingers 2040 may include an intermediate portion 2046 comprising a bushing 2048 disposed within a slot of the two or more slots 2032 of the slotted cam 2030. Further, the fingers 2040 may have a lower portion 2050 comprising a sample contact surface 2052, which may be disposed below the slotted cam 2030 and at a distal end of the fingers 2040.

Additionally, the device 2000 may include a lower housing 2060. The lower housing 2060 surrounds the driveshaft 2004, the slip clutch 2010, the pivot housing 2020, the slotted cam 2030, the upper portion 2042 of the fingers 2040, and the intermediate portion 2046 of the fingers 2040. The lower housing 2060 may include a lower portion 2050 or a bottom plate 2061, which has apertures for accommodating the fingers 2040. In some aspects, the slotted cam 2030 is fitted within, but does not contact the lower housing 2060. As a result, rotation of the driveshaft 2004 may rotate the slotted cam 2030 within the lower housing 2060.

Additionally, the pivot housing 2020 may be affixed to an interior surface of the lower housing 2060. Accordingly, because the pivot housing 2020 is affixed to the rotating portion 2014 of the slip clutch 2010, when the rotating portion 2014 of the slip clutch 2010 rotates, the lower housing 2060 may also rotate. Further, the lower housing 2060 (and each of the parts therein) and the lower portion 2050 of the fingers 2040 may form an end-effectuator 2062. The end-effectuator 2062 is the portion of the device 2000 that operates to grip and rotate the sample tube 2003.

In one aspect, upon receiving rotational force in a first direction from the motor 2002, the driveshaft 2004 rotates the slotted cam 2030 in the first direction. The rotation of the slotted cam 2030 in the first direction causes the bushings 2048 of the two or more fingers 2040 to move from a first position within the two or more slots 2032 toward a second position within the two or more slots 2032. Further, the first position within the two or more slots 2032 is distal from the center of the slotted cam 2030, and the second position within the two or more slots 2032 is proximate the center of the slotted cam 2030.

Accordingly, as shown in FIG. 16, when the slotted cam 2030 is rotated, the bushings 2048 are forced inward. As a result, the movement of the bushings 2048 of the two or more fingers 2040 from the first position within the two or more slots 2032 to the second position within the two or more slots 2032 causes the lower portion 2050 of the two or more fingers 2040 to move toward a center point between a terminal end of the two or more fingers 2040. Further, the inward force at the bushings 2048 causes the sample contact surfaces 2052 of the fingers 2040 to move closer together in a gripping motion. As can be appreciated, because the upper portion 2042 of the fingers 2040 are retainably mounted in the pivot housing 2020, the space between the fingers 2040 the upper portion 2042 remains the same during rotation of the slotted cam 2030. Accordingly, the slotted cam 2030 cinctures the fingers 2040 in order to provide gripping force on the sample tube 2005. In one aspect, the device 2000 includes four fingers 2040 equally spaced apart and retained in the pivot housing 2020.

Upon encountering a resistance force, the motor 2002 may increase rotational torque, thereby overcoming the slip clutch 2010. The resistance force may be caused, for example, by the sample contact surfaces 2052 contacting the sample tube 2003, or an end of the two or more slots 2032 proximate the center of the slotted cam 2030. The slip clutch 2010 has a preset torque setting. Because the fingers 2040 are retained in the pivot housing 2020, which is affixed to the rotating portion 2014 of the slip clutch 2010, when the resistance force is encountered by the fingers 2040, the rotational force is imparted to the pivot housing 2020 and the rotating portion 2014 of the slip clutch 2010. The increased rotational torque is above a preset torque setting, which overcomes the slip clutch 2010 and allows the end-effectuator 2062 to rotate. As a result, the sample tube 2003 may be continually rotated for analysis.

In one aspect, the device 2000 further comprises a sensor 2008 for detecting a rotation of the lower housing 2060. The rotation of the lower housing 2060 may be measured, for example, from a home position to the resistance force. Accordingly, the sensor 2008 may detect a distance from the home position to, for example, a sample tube 2003 corresponding to the resistance force. As a result, a diameter of the sample tube 2003 may be determined based on the measured rotation. The diameter of the sample tube 2003 may be determined, for example, using an optical encoder, which may be integrated with the motor 2002 and located in the upper housing 2001.

In another embodiment, a sample tube 2003 gripping and rotation device 2000 for use in an automated blood sample processing system 210 is provided. The device 2000 may comprise: an upper housing 2001; a vertically-oriented motor 2002 disposed within the upper housing 2002; and a vertically-oriented driveshaft 2004 extending downward from the motor 2002 and through the upper housing 2001. The device 2000 may also include a lower housing 2060; a slip clutch 2010 positioned about and spaced apart from the driveshaft 2004, the slip clutch 2010 comprising: a fixed portion 2012 affixed to the upper housing 2001; and a rotating portion 2014 disposed within the lower housing 2060. Further, the device 2000 may include a pivot housing 2020 positioned about and spaced apart from the driveshaft 2004 and affixed to the rotating portion 2014 of the slip clutch 2010 and an interior surface of the lower housing 2060. Additionally, the device 2000 may comprise a horizontally-oriented slotted cam 2030 disposed below the pivot housing 2020 and coupled to a distal end of the driveshaft 2004, the slotted cam 2030 comprising: two or more slots 2032 extending diagonally outward from the center of the slotted cam 2030. Further, the device 2000 may include two or more vertically-oriented fingers 2040, each finger 2040 of the two or more fingers 2040 comprising: an upper portion 2042 comprising a pivot 2044 retained in the pivot housing 2020; an intermediate portion 2046 comprising a bushing 2048 disposed within a slot of the two or more slots 2032 of the slotted cam 2030; and a lower portion 2050 comprising a sample contact surface 2052 disposed below the slotted cam 2030. Additionally, the device 2000 may include a sensor 2008 for detecting a rotation of the lower housing 2060.

Similar to the embodiments described hereinabove, rotation of the motor 2002 in a first direction causes the sample contact surfaces 2052 of the two or more fingers 2040 to move toward a center point between a terminal end of the two or more fingers 2040. Accordingly, the two or more fingers 2040 move in a gripping-type motion when the motor 2002 rotates in the first direction. Further, upon reaching a resistance point in the first direction, the motor 2002 is configured to increase a rotational torque of the rotation in the first direction to overcome the slip clutch 2010. Accordingly, upon the slip clutch 2010 being overcome, an end-effectuator 2062 of the device 2000 is continually rotated in the first direction. Accordingly, when the rotational torque is increased, the entire end-effectuator 2062 may rotate, along with a sample tube 2003 retained between the two or more fingers 2040.

Further, the sensor 2008 may be configured to detect a rotation of the lower housing 2060 from a first position to the resistance point. In some aspects, the rotation corresponds to a tube width of a sample tube 2003. Additionally, the motor 2002 may rotate and a second direction, the second direction being opposite to the first direction. Rotation of the motor 2002 in the second direction may act to reverse the gripping pressure caused by rotation in the first direction. Accordingly, rotation in the second direction causes the sample contact surfaces 2052 of the two or more fingers 2040 to move away from the center point between the terminal end of the two or more fingers 2040. As a result, rotation in the second direction releases the gripping pressure on the sample tube 2003, thereby allowing the tube to be retained in a sample tube holder 2005 when the tube is returned to the sample tube holder 2005.

In another embodiment, a sample tube 2003 gripping and rotation device 2000 for use in a specimen integrity monitor is provided. The device 2000 may comprise: an upper housing 2001; a vertically-oriented motor 2002 disposed within the upper housing 2002; and a vertically-oriented driveshaft 2004 extending downward from the motor 2002 and through the upper housing 2001. The device 2000 may also include a lower housing 2060; a slip clutch 2010 positioned about and spaced apart from the driveshaft 2004, the slip clutch 2010 comprising: a fixed portion 2012 affixed to the upper housing 2001; and a rotating portion 2014 disposed within the lower housing 2060. Further, the device 2000 may include a pivot housing 2020 positioned about and spaced apart from the driveshaft 2004 and affixed to the rotating portion 2014 of the slip clutch 2010 and an interior surface of the lower housing 2060. Additionally, the device 2000 may comprise a horizontally-oriented slotted cam 2030 disposed below the pivot housing 2020 and coupled to a distal end of the driveshaft 2004, the slotted cam 2030 comprising: two or more slots 2032 extending diagonally outward from the center of the slotted cam 2030. Further, the device 2000 may include two or more vertically-oriented fingers 2040, each finger 2040 of the two or more fingers 2040 comprising: an upper portion 2042 comprising a pivot 2044 retained in the pivot housing 2020; an intermediate portion 2046 comprising a bushing 2048 disposed within a slot of the two or more slots 2032 of the slotted cam 2030; and a lower portion 2050 comprising a sample contact surface 2052 disposed below the slotted cam 2030. Additionally, the device 2000 may include a sensor 2008 for detecting a rotation of the lower housing 2060.

In one aspect, the device 2000 comprises a controller 2006 for controlling the motor 2002 and for receiving sensor 2008 information from the sensor 2008. In some aspects, the controller 2006 is communicatively coupled to a specimen integrity monitor. In additional aspects, the controller 2006 is configured to cause the motor 2002 to continually rotate in a first direction until an indication is received from the specimen integrity monitor.

In an additional aspect, upon receiving the indication from the specimen integrity monitor, the controller 2006 is configured to cause the motor 2002 to rotate in a second direction. Further, in one aspect, the indication is communicated when processing of a sample by the specimen integrity monitor is complete. Accordingly, the device 2000 may rotate a sample tube 2003 during processing by the specimen integrity monitor, which may allow the specimen integrity monitor to capture sensor 2008 data from any number of angles of the tube. As a result, the sensor 2008 data may include data for the entire sample.

Many different arrangements of the various components depicted, as well as components not shown, are possible without departing from the spirit and scope of the present invention. Embodiments of the invention have been described with the intent to be illustrative rather than restrictive. Alternative embodiments may become apparent to those skilled in the art that do not depart from its scope. A skilled artisan may develop alternative means of implementing the aforementioned improvements without departing from the scope of the invention.

Further, it may be understood that certain features and subcombinations are of utility, may be employed without reference to other features and subcombinations, and are contemplated within the scope of the claims. Not all steps listed in the various figures need be carried out in the specific order described.

What is claimed:

1. A sample tube gripping and rotation device for use in an automated blood sample processing system, the device comprising:
    an upper housing;
    a vertically-oriented motor disposed within the upper housing;
    a vertically-oriented driveshaft extending downward from the motor and through the upper housing;
    a lower housing;
    a slip clutch positioned about and spaced apart from the driveshaft, the slip clutch comprising:
        a fixed portion affixed to the upper housing; and
        a rotating portion disposed within the lower housing;
    a pivot housing positioned about and spaced apart from the driveshaft and affixed to the rotating portion of the slip clutch and an interior surface of the lower housing;
    a horizontally-oriented slotted cam disposed below the pivot housing and coupled to a distal end of the driveshaft, the slotted cam comprising:
        two or more slots extending diagonally outward from the center of the slotted cam;
    two or more vertically-oriented fingers, each finger of the two or more fingers comprising:
        an upper portion comprising a pivot retained in the pivot housing;
        an intermediate portion comprising a bushing disposed within a slot of the two or more slots of the slotted cam; and
        a lower portion comprising a sample contact surface disposed below the slotted cam; and
    a sensor for detecting a rotation of the lower housing.

2. The device of claim 1, wherein rotation of the motor in a first direction causes the sample contact surfaces of the two or more fingers to move toward a center point between a terminal end of the two or more fingers.

3. The device of claim 2, wherein upon reaching a resistance point in the first direction, the motor is configured to increase a rotational torque of the rotation in the first direction to overcome the slip clutch.

4. The device of claim 3, wherein upon the slip clutch being overcome, an end-effectuator of the device is continually rotated in the first direction.

5. The device of claim 3, wherein the rotation of the lower housing from a first position to the resistance point is detected by the sensor and corresponds to a tube width of a sample tube.

6. The device of claim 2, wherein rotation of the motor in a second direction causes the sample contact surfaces of the two or more fingers to move away from the center point between the terminal end of the two or more fingers.

* * * * *